(12) United States Patent
Hua et al.

(10) Patent No.: US 9,550,817 B2
(45) Date of Patent: Jan. 24, 2017

(54) MEN1 GENE FOR DIAGNOSIS AND TREATMENT OF DIABETES

(75) Inventors: Xianxin Hua, Winnewood, PA (US); Ya-Xiong Chen, Charlottesville, VA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 12/324,473

(22) Filed: Nov. 26, 2008

(65) Prior Publication Data
US 2009/0181917 A1 Jul. 16, 2009

Related U.S. Application Data

(63) Continuation-in-part of application No. PCT/US2007/012557, filed on May 29, 2007.

(60) Provisional application No. 60/808,556, filed on May 26, 2006, provisional application No. 60/881,153, filed on Jan. 19, 2007.

(51) Int. Cl.
| | | |
|---|---|---|
| *C12N 15/11* | (2006.01) | |
| *C07H 21/02* | (2006.01) | |
| *A61K 38/00* | (2006.01) | |
| *C07K 7/00* | (2006.01) | |
| *C07K 7/08* | (2006.01) | |
| *C07K 14/47* | (2006.01) | |

(52) U.S. Cl.
CPC ................ *C07K 14/4713* (2013.01)

(58) Field of Classification Search
None
See application file for complete search history.

(56) References Cited

U.S. PATENT DOCUMENTS

2004/0053345 A1 3/2004 Yamauchi et al.

OTHER PUBLICATIONS

Smart (PloS Biology 14(2): e39, Feb. 2006).*
Jetton et al (Diabetes 54: 2294-2304, 2005, see abstract).*
Grossman et al (PloS One 5(1): e8749, 2010).*
Opalinska et al (Nature Reviews Drug Discovery, 2002, vol. 1, pp. 503-514).*
Caplen (Expert Opin. Biol. Ther. 2003, vol. 3, pp. 575-586).*
Check (Nature, 2003, vol., 425, pp. 10-12).*
Grossman et al (Neuro-Oncology 6: 32-40, 2004).*
Read et al (Adv. Gen. 53:19-46, 2005).*
Cejka et al (Clinical Science 110: 47-58, 2006).*
Nguyen et al (Curr. Opin. Mol. Ther. 10(2): 158-167, 2008).*
Moulder et al (Clin. Cancer Res. 14(23): 7909-7916, 2008).*
Rudin et al (J. Clin. Oncol.26(6): 870-876, 2008).*
Crabtree et al (Molecular and Cellular Biology, 23(17): 6075-6085).*
Sorell et al (Biotechnology Advances 23 (2005) 431-469).*
Vazquez et al (Proc. Nat. Acad. Sci. USA 98(15): 8403-8410).*
Vasquez et al (Science 2000;290:530-3).*
Balasubramanian et al (Adv. Exp. Med. Biol. 668: 105-115, 2009).*
Karnik et al (Proc Natl Acad Sci U S A. Oct. 11, 2005;102(41):14659-64. Epub Sep. 29, 2005).*
Karnik et al (Proc Natl Acad Sci U S A. Oct. 11, 2005;102(41):14659-64. Epub Sep. 29, 2005), supporting Figure 4.*
Karnik et al (Proc Natl Acad Sci U S A. Oct. 11, 2005;102(41):14659-64. Epub Sep. 29, 2005) Legend or supporting Figure 4.*
Kaji et al (Proc Nat Acad Sci USA 98: 3837-3842, Mar. 27, 2001).*
Bain et al (Diabetes 53:2190-2194, 2004).*
Bertolino et al (Cancer Res. 63: 4836-4841, 2003c).*
Fiaschi-Taesch et al (Diabetes 59: 1926-1936, 2010).*
Efrat (Rev. Diabet. Studies 5(2): 116-122, 2008).*
Crabtree et al (Proc. Nat. Acad. USA 98(3): 1118-1123, 2001).*
Marx (Ann. Int. Med. 129(6): 484-495, 1998).*
Perren et al (J. Clin. Endocrinol. Metab. 92(3): 1118-1128, 2007).*
Nielsen et al, "Synthesis of 29-O,39-C-linked bicyclic nucleosides and bicyclic oligonucleotides ", 1997 J. Chem. Soc. Perkin Trans. 1, 3423.
Koshkin et al, "Novel convenient syntheis of LNA [2.2.1]Bicyclo Nucleosides", 1998, Tetrahedron Letters 39, 4381.
Singh & Wengel "Universality of LNA-mediated high-affinity nucleic acid recognition", 1998 Chem. Commun. 1247.
Singh et al, "LNA (locked nucleic acids): synthesis and high-affinity nucleic acid recognition ", 1998 Chem. Commun. 455.
Ramiya, "Reversal of insulin-dependent diabetes using islets generated in vitro from pancreatic stem cells" Nature Medicine, 2000 (6):278-82.
Jones, "Cell-based treatments for diabetes", Drug Discov Today 2008 (19-20): 888-93.
Scott and Smith, "Discovering peptide ligands using epitope libraries", Science, 249:386-390 (1990).
Cwirla et al., "Peptides on phage: A vast library of peptides for identifying ligands" Proc. Natl. Acad. Sci., 87:6378-6382 (1990).
Devlin et al., "Random Peptide Libraries: A Source of Specific Protein Binding Molecules" Science, 249:404-406 (1990).
Lam et al., "Rational Design of Potent, Bioavailable, Nonpeptide Cyclic Ureas as HIV Protease Inhibitors" Science 263:380-384 (1994).
Wlodawer et al., " Structure-Based Inhibitors of HIV-1 Protease" Ann. Rev. Biochem. 62:543-585 (1993).
Appelt, "Crystal structures of HIV-1 protease-inhibitor complexes", Perspectives in Drug Discovery and Design 1:23-48 (1993);.
Erickson, "Design and structure of symmetry-based inhibitors of HIV-1 protease", Perspectives in Drug Discovery and Design 1: 109-128 (1993).
Kraulis, "Molscript: a program to produce both detailed and schematic plots of protein structures", J. Appl Crystallogr. 24:946-950 (1991).
Marx S., et al, "Multiple endocrine neoplasia Type I", http://www.endocrine.niddk.nih.gov/pubs/men1/men1.htm, Mar. 2006.
Sayo et al., "The multiple endocrine neoplasia Type I gene product, menin, inhibits insulin production in rat insulinoma cells", Endocrinology, 2002, vol. 143, No. 6, pp. 2437-2440.

\* cited by examiner (Continued)

Primary Examiner — Richard Schnizer
(74) Attorney, Agent, or Firm — Mark S. Cohen; Pearl Cohen Zedek Latzer Baratz LLP

(57) ABSTRACT

This invention relates to the inhibition of expression or function of Men1 gene or its encoded proteins for the purpose of treating diabetes and screening and researching agents capable of inhibiting expression or function of Men1 gene or its encoded proteins for use in the treatment and diagnosis of diabetes.

5 Claims, 22 Drawing Sheets

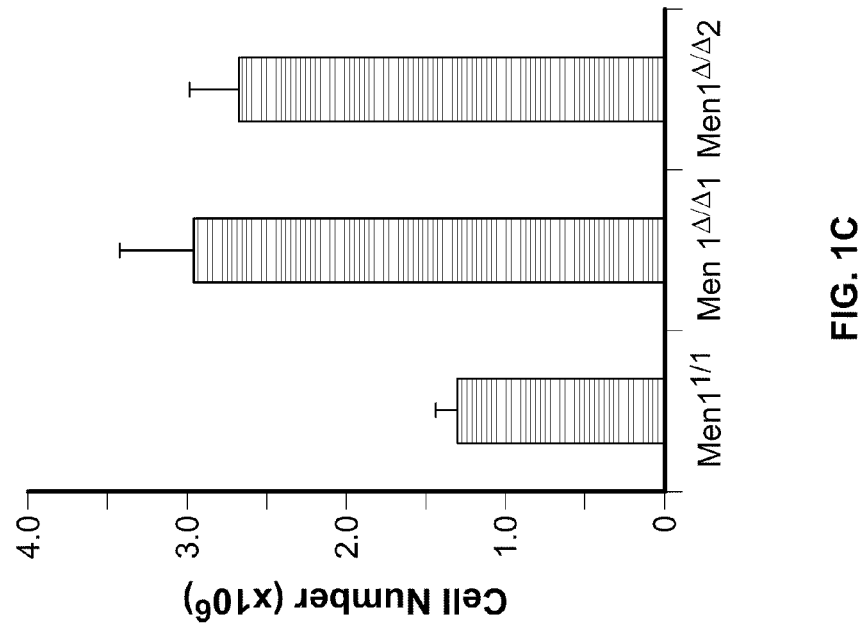
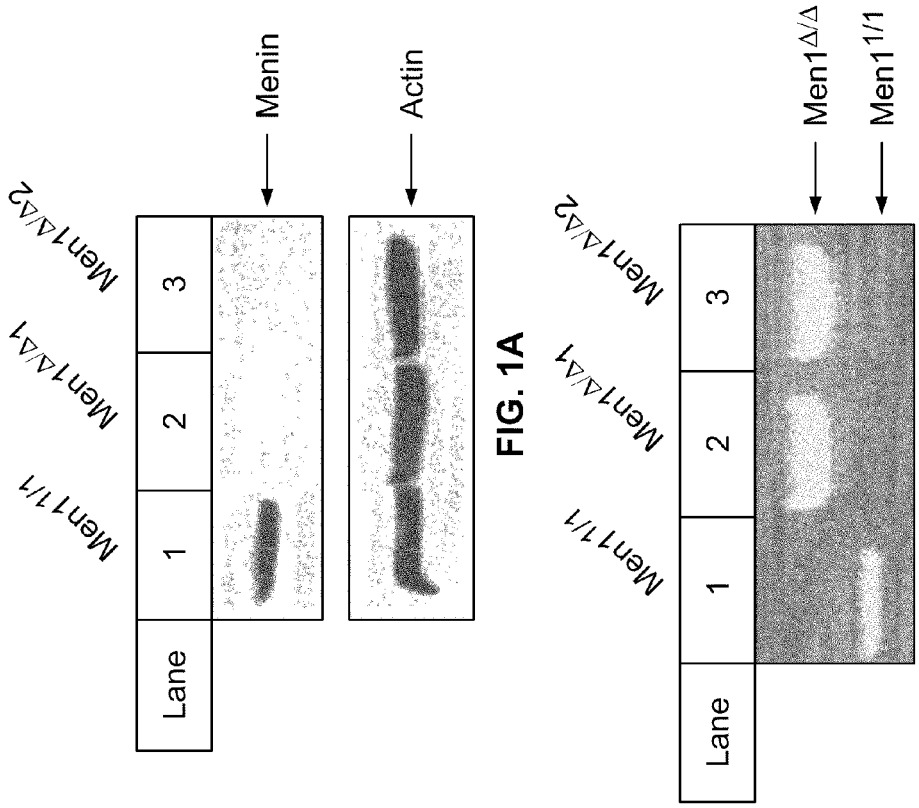

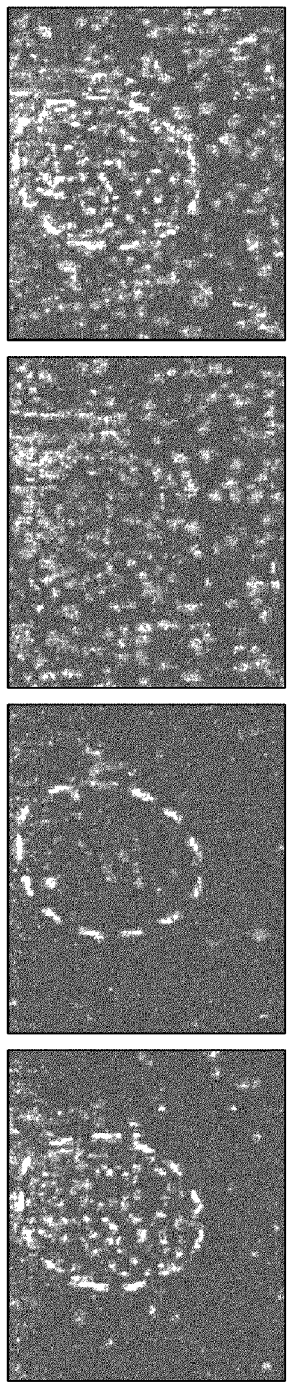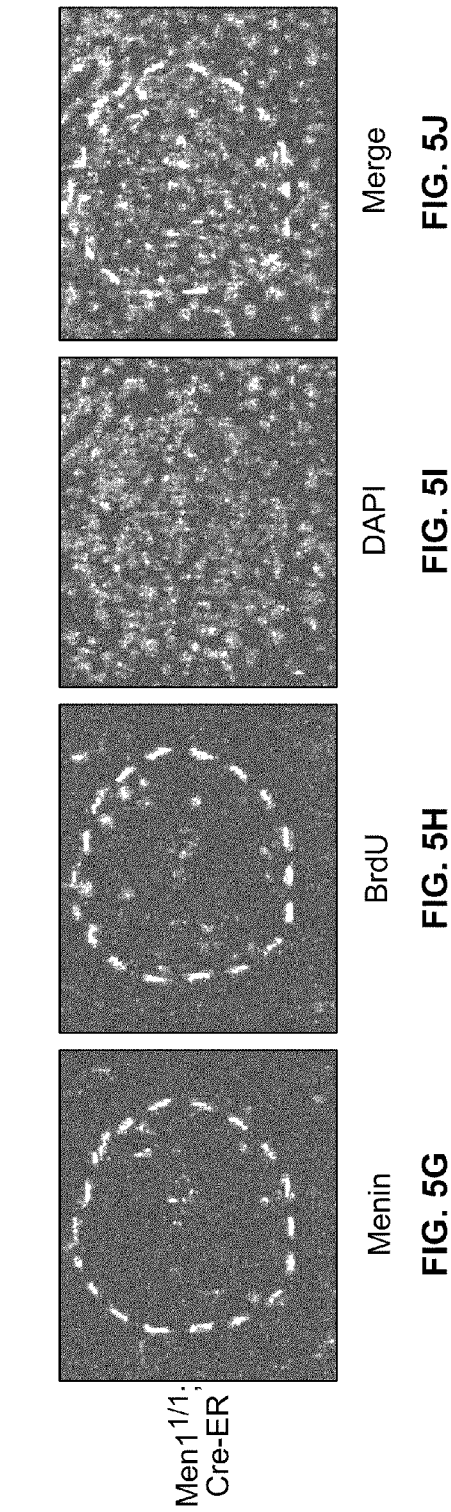

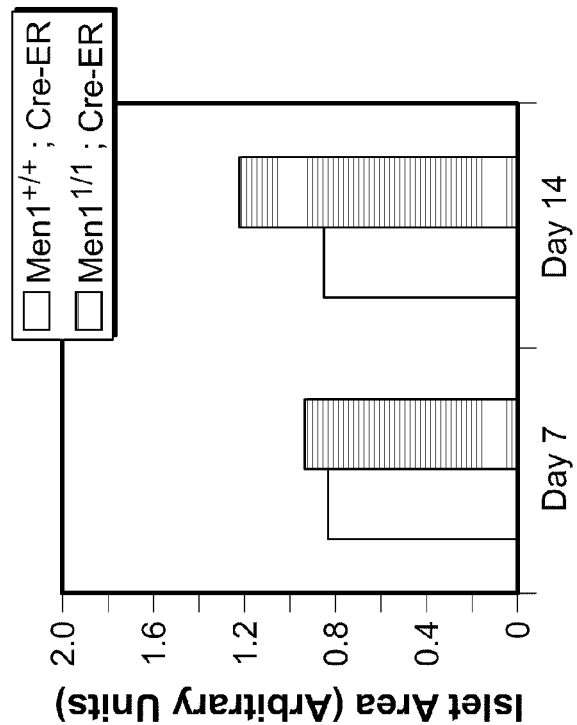
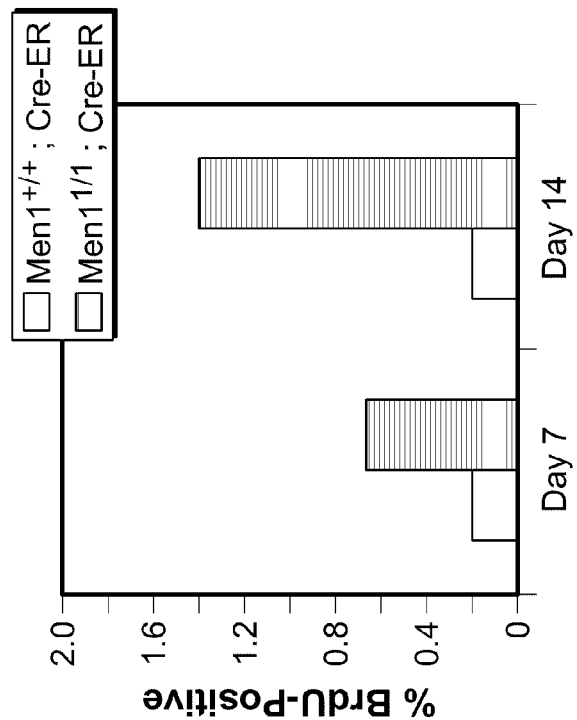
FIG. 7A
FIG. 7B

| Gender | mwtCre-TAMX | Gender | MI/ICre-oil | Gender | MI/ICre-TAMX |
|---|---|---|---|---|---|
| m | 437.703 | m | 254.260 | f | 212.042 |
| f | 165.785 | m | 197.443 | f | 137.351 |
| f | 170.877 | m | 175.702 | m | 220.105 |
| m | 515.473 | m | 107.474 | m | 86.001 |
| m | 195.414 | f | 139.898 | m | 149.322 |
| m | 235.998 | f | 183.609 | m | 213.387 |
| m | 212.807 | f | 124.196 | m | 262.087 |
| m | 214.256 | f | 190.399 | m | 162.947 |

FIG. 8

| Gender | mwtCre-TAMX | Gender | MI/ICre-oil | Gender | MI/ICre-TAMX |
|---|---|---|---|---|---|
| m | 263.020 | m | 217.080 | f | 149.130 |
| f | 174.960 | m | 198.360 | f | 164.560 |
| f | 172.710 | m | 114.110 | m | 145.840 |
| m | 165.080 | m | 183.630 | m | 173.920 |
| m | 178.890 | f | 140.626 | m | 162.947 |
| m | 208.459 | f | 209.038 | m | 198.023 |
| m | 167.295 | f | 173.383 | m | 181.789 |
| m | 164.396 | f | 184.688 | m | 200.922 |

FIG. 10A

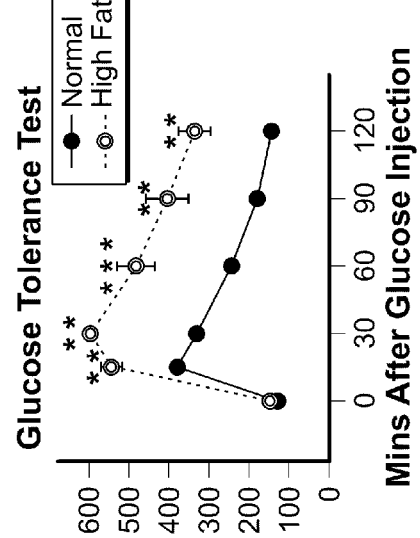
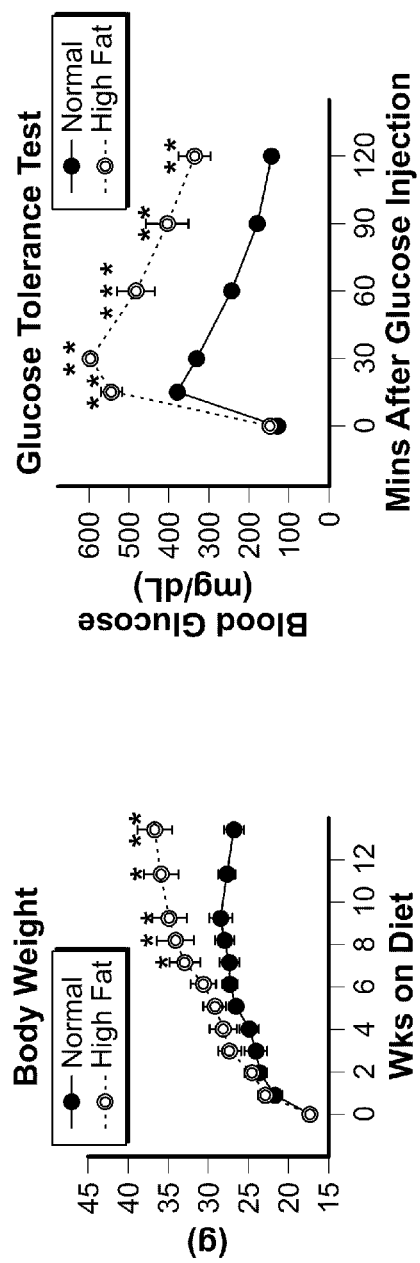
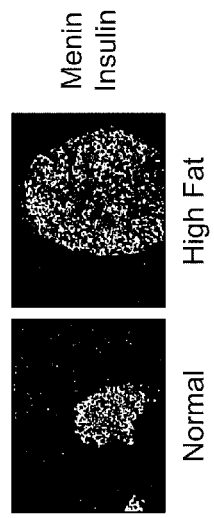
FIG. 13A
FIG. 13B
FIG. 13C
FIG. 13D

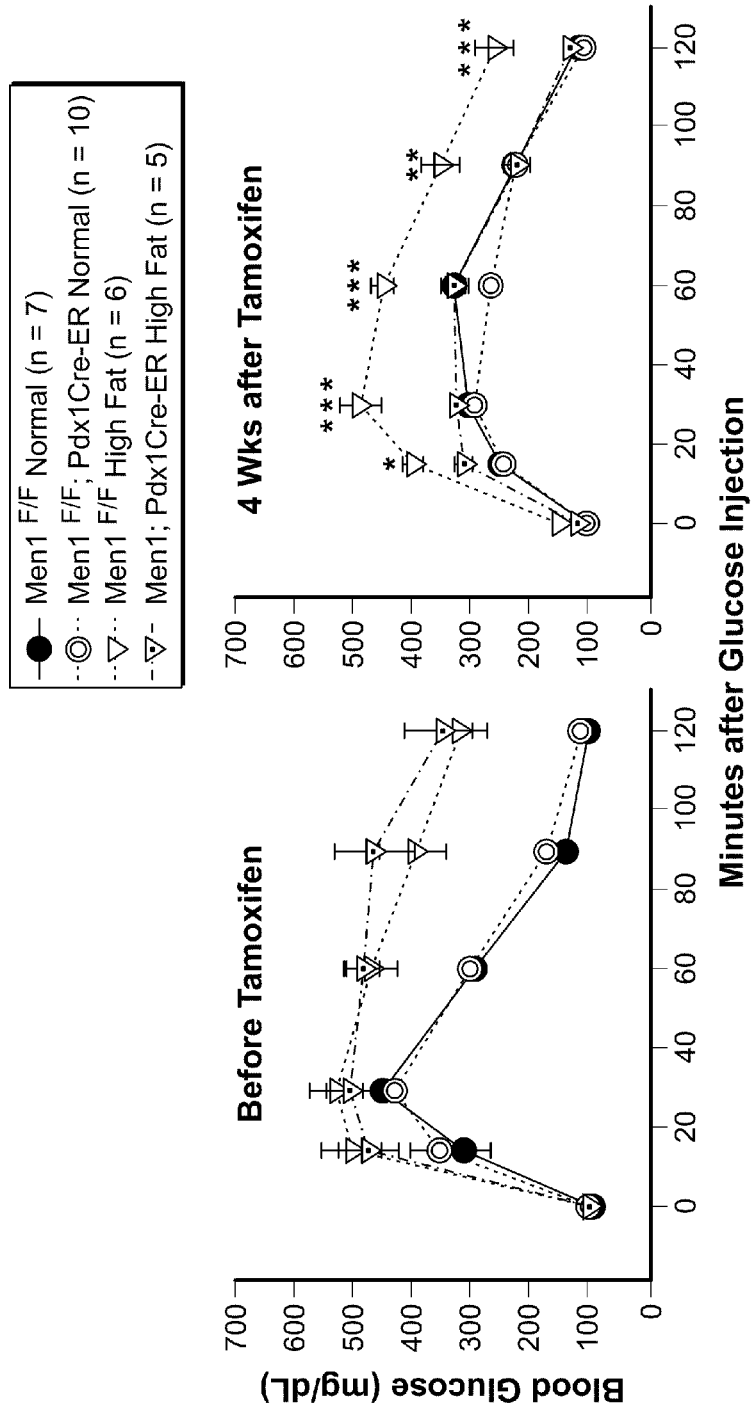

*MEN1* GENE FOR DIAGNOSIS AND TREATMENT OF DIABETES

CROSS REFERENCE TO RELATED APPLICATIONS

This application is a Continuation-In-Part of PCT International Application No. PCT/US07/12557, International Filing Date May 29, 2007, claiming priority of United States Provisional Patent Applications, 60/808,556, filed May 26, 2006, and 60/881,153, filed Jan. 19, 2007, all which are incorporated herein by reference in their entirety.

FIELD OF INVENTION

This invention is directed to the role of Men1 gene in the treatment of diabetes. Specifically, the invention relates to the inhibition of expression or function of Men1 gene or its encoded proteins including menin for the purpose of treating diabetes and screening and researching agents capable of inhibiting expression or function of Men1 gene or its encoded proteins for use in treating diabetes.

BACKGROUND OF THE INVENTION

Diabetes mellitus (DM) describes several syndromes of abnormal carbohydrate metabolism, characterized by hyperglycemia. It is associated with a relative or absolute impairment in insulin secretion, along with varying degrees of peripheral resistance to the action of insulin. The chronic hyperglycemia of diabetes is associated with long-term damage, dysfunction, and failure of various organs, especially the eyes, kidneys, nerves, heart, and blood vessels.

There are two major forms of diabetes: Type 1 diabetes, also referred to as insulin-dependent diabetes; and Type 2 diabetes, also referred to as noninsulin dependent diabetes. When inadequate amounts of insulin are present to compensate for insulin resistance and adequately control glucose, a state of impaired glucose tolerance develops. In a significant number of individuals, the plasma glucose level rises, resulting in the clinical state of diabetes. Insulin stimulates glucose uptake by skeletal muscle and adipose tissues primarily through translocation of the glucose transporter 4 from the intracellular storage sites of the cell surface Diabetes is often associated with high fat diet and obesity. The majority of diabetic patients are treated either with hypoglycemic agents which act by stimulating release of insulin from beta cells, or with agents that enhance the tissue sensitivity of the patients towards insulin, or with insulin.

Multiple endocrine neoplasia type 1 (MEN1) is a dominantly inherited tumor syndrome that results from the mutation of the tumor suppressor gene Men1, which encodes menin. Menin interacts with multiple proteins that play critical roles in the regulation of cell proliferation, including JunD, Smad 3, and activator of S-phase kinase. Activator of S-phase kinase is the crucial regulatory factor for protein kinase cdc7 that is required for initiation of DNA replication and menin functionally represses the activity of activator of S-phase kinase. In addition, menin interacts with a protein complex containing the mixed lineage leukemia protein and up-regulates transcription of various target genes, including the cyclin-dependent kinase (CDK) inhibitors $p27^{Kip1}$ and $p18^{Ink4c}$, in transformed fibroblasts and insulinoma cells. Whereas these observations provide a potential mechanistic link between menin and cell cycle regulation, a direct link between menin function and cell cycle progression has not been established. An obstacle to answering this question has been the lack of synchronizable cells in which Men1 can be conditionally inactivated in vitro so that the effect of Men1 deletion on the cell cycle progression can be examined.

Mouse models have greatly increased understanding of molecular pathology of the MEN1 syndrome. Tumors derived from mice heterozygous for Men1 display loss of heterozygosity, confirming the role of menin as a bona fide tumor suppressor. Tumors arise in the parathyroid, pituitary, and pancreatic islet cells from the mice in which Men1 is conditionally inactivated in these respective organs, establishing an important role for menin in suppressing tumor development in endocrine organs. However, because the excision of Men1 is not under temporal control in these mice, it is challenging to study the acute effects of deletion of Men1 on proliferation of pancreatic islet cells. Thus, although tumor cells in insulinomas of the mice display enhanced cell proliferation as shown by 5'-bromo-2'-deoxyuridine-5'-triphosphate (BrdUrd) uptake, it is difficult to determine how soon after Men1 deletion, increased islet cell proliferation occurs. If increased islet proliferation is an acute consequence of Men1 deletion, then this would suggest that loss of menin-mediated repression of cell proliferation is at least in part responsible for the early events of islet cell proliferation observed in MEN1.

While current drug therapy may provide reduction in blood sugar, it often promotes obesity as well as, in the long term, may lead to accelerated exhaustion of the endogenous production of insulin in diabetics Accordingly, a need exists for improved methods and compositions for treating various forms of diabetes.

SUMMARY OF THE INVENTION

In one embodiment, the invention provides a method of treating diabetes in a subject, comprising the step of contacting a pancreatic cell of said subject with an effective amount of an agent capable of inhibiting the expression or function of Men1 gene or its encoded proteins, whereby the inhibition of expression or function of Men1 gene or its encoded proteins results in increasing insulin production in said pancreatic cell, thereby reducing blood sugar level.

In another embodiment, the invention provides a composition for the treatment of diabetes in a subject, comprising an effective amount of an agent capable of inhibiting the expression or function of Men1 gene or its encoded proteins in said subject, resulting in selective proliferation of pancreatic islet cells.

In one embodiment, the invention provides a method of increasing proliferation of pancreatic β-cells in a subject, comprising the step of inhibiting expression or function of Men1 gene or its encoded proteins in the pancreas of said subject.

In another embodiment, the invention provides a method of screening for therapeutic agents for the treatment of diabetes in a diabetic human subject, comprising the step of: contacting a pancreatic beta cell of said subject with the candidate therapeutic agent; and analyzing for the expression or function of Men1 gene or its encoded proteins in said contacted cell, wherein inhibition of the expression or function of Men1 gene in said pancreatic cell indicates the candidate therapeutic agent is effective in treating diabetes.

In one embodiment, the invention provides a method of inducing selective proliferation of islet cells, comprising the step of contacting said islet cells with an agent capable of inhibiting the expression or function of Men1 gene or its encoded proteins in pancreatic cells, thereby resulting in selective proliferation of islet cells.

In another embodiment, the invention provides a method of inducing CDK2 activity in a cell, comprising the step of contacting the cell with an agent capable of inhibiting the expression or function of Men1 gene or its encoded proteins, thereby reducing $p18^{Ink4c}$ and $p27^{Kip1}$, expression or function, thereby resulting in upregulation of CDK2 activity in a cell.

In another embodiment, the invention provides a method to identify an antagonist ligand of menin, comprising the steps of: contacting a menin protein with a candidate antagonist ligand, under conditions wherein, in the absence of said candidate antagonist ligand, said menin protein is active; and detecting concentration or activity of said menin protein or at least one protein that is regulated by said menin protein when said menin protein is not inactivated, whereby reduction in concentration or activity of said menin protein or said at least one protein indicates that said candidate antagonist ligand is a menin antagonist In another embodiment, the invention provides a method of using a three-dimensional structure of menin protein in a drug screening assay, comprising the steps of: selecting a potential drug by performing rational drug design based on said three-dimensional structure; contacting the potential drug with a first polypeptide comprising an amino acid sequence having at least 75% homology to a first predetermined region of the menin; and detecting the binding affinity of the potential drug with said first polypeptide, whereby a potential drug is selected as a drug if the potential drug binds to said first polypeptide.

In another embodiment, provided herein is a method of reducing blood sugar in a diabetic subject, comprising the step of administering to the subject an agent capable of inhibiting the expression or function of Men1 gene or its encoded proteins in pancreatic cells, thereby resulting in reduction of blood sugar in the diabetic subject.

In one embodiment, the invention provides a method of treating a high fat diet associated diabetes in a subject, comprising the step of administering to a subject with an effective amount of an agent capable of inhibiting the expression or function of a Men1 gene or a protein encoded thereby, whereby the inhibition of expression or function of said Men1 gene or said protein reduces blood sugar level of said subject. In an embodiment, the high fat diet associated diabetes is a Type 2 diabetes.

In another embodiment, the invention provides a method of treating a high fat diet associated diabetes in a subject, comprising the step of contacting a cell of said subject with an effective amount of an agent capable of inhibiting the expression or function of a Men1 gene or a protein encoded thereby, whereby the inhibition of expression or function of said Men1 gene or said protein reduces blood sugar level of said subject. In an exemplary embodiment, the cell is a pancreatic stem cell.

In another embodiment, the invention provides a pancreatic stem cell for treating a high fat diet associated diabetes in a subject, comprising an agent capable of inhibiting the expression or function of a Men1 gene or a protein encoded thereby, whereby the inhibition of expression or function of said Men1 gene or said protein reduces blood sugar level of said subject.

In another embodiment, the invention provides a pharmaceutical composition comprising an effective amount of an agent capable of inhibiting the expression or function of a Men1 gene or a protein encoded thereby in a high fat diet associated diabetic subject and a pharmaceutically acceptable carrier.

In another embodiment, the invention provides a method of screening for therapeutic agents for the treatment of a high fat diet associated diabetes in a subject, comprising the step of: contacting a pancreatic β-cell with a candidate therapeutic agent; and analyzing for the expression or function of Men1 gene or its encoded proteins in said cell, wherein inhibition of the expression or function of Men1 gene or its encoded proteins in said pancreatic cell indicates that the candidate therapeutic agent is effective in treating said high fat diet associated diabetes.

In another embodiment, the invention provides a method of reducing blood sugar in a high fat diet associated diabetic subject, comprising the step of administering to the subject an agent capable of inhibiting the expression or function of Men1 gene or its encoded proteins in a pancreatic cell of said diabetic subject, thereby resulting in reduction of blood sugar in the diabetic subject.

In one embodiment, the invention provides a method of treating an obesity associated diabetes in a subject, comprising the step of administering to a subject with an effective amount of an agent capable of inhibiting the expression or function of a Men1 gene or a protein encoded thereby, whereby the inhibition of expression or function of said Men1 gene or said protein reduces blood sugar level of said subject. In an exemplary embodiment, the obesity associated diabetes is a Type 2 diabetes.

In another embodiment, the invention provides a method of treating an obesity associated diabetes in a subject, comprising the step of contacting a cell of said subject with an effective amount of an agent capable of inhibiting the expression or function of a Men1 gene or a protein encoded thereby, whereby the inhibition of expression or function of said Men1 gene or said protein reduces blood sugar level of said subject. In an exemplary embodiment, the cell is a pancreatic stem cell.

In another embodiment, the invention provides a pancreatic stem cell for treating an obesity associated diabetes in a subject, comprising an agent capable of inhibiting the expression or function of a Men1 gene or a protein encoded thereby, whereby the inhibition of expression or function of said Men1 gene or said protein reduces blood sugar level of said subject.

In another embodiment, the invention provides a pharmaceutical composition comprising an effective amount of an agent capable of inhibiting the expression or function of a Men1 gene or a protein encoded thereby in an obesity associated diabetic subject and a pharmaceutically acceptable carrier.

In another embodiment, the invention provides a method of screening for therapeutic agents for the treatment of an obesity associated diabetes in a subject, comprising the step of: contacting a pancreatic β-cell with a candidate therapeutic agent; and analyzing for the expression or function of Men1 gene or its encoded proteins in said cell, wherein inhibition of the expression or function of Men1 gene or its encoded proteins in said pancreatic cell indicates that the candidate therapeutic agent is effective in treating said obesity associated diabetes.

In another embodiment, the invention provides a method of reducing blood sugar in an obesity associated diabetic subject, comprising the step of administering to the subject an agent capable of inhibiting the expression or function of Men1 gene or its encoded proteins in a pancreatic cell of said diabetic subject, thereby resulting in reduction of blood sugar in the diabetic subject.

In another embodiment, the invention provides a method enhancing glucose-sensing in a subject, comprising the step of administering to a subject with an effective amount of an agent capable of inhibiting the expression or function of a Men1 gene or a protein encoded thereby, whereby the inhibition of expression or function of said Men1 gene or said protein enhances glucose-sensing in said subject. In an embodiment, the method enhances glucose-sensing via increased expression of a glucose transporter ("GLUT") or a glucokinase ("GK").

In another embodiment, the invention provides a method of enhancing glucose-sensing in a subject, comprising the step of contacting a cell of said subject with an effective amount of an agent capable of inhibiting the expression or function of a Men1 gene or a protein encoded thereby, whereby the inhibition of expression or function of said Men1 gene or said protein enhances glucose-sensing in said subject. In an exemplary embodiment, the cell is a pancreatic stem cell.

In another embodiment, the invention provides a pancreatic stem cell for enhancing glucose-sensing in a subject, comprising an agent capable of inhibiting the expression or function of a Men1 gene or a protein encoded thereby, whereby the inhibition of expression or function of said Men1 gene or said protein enhances glucose-sensing in said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which:

FIG. 1 shows that ablation of Men1 in MEFs results in increased cell proliferation in vitro. A) Cre-mediated excision of the Men1 flanked by the two lox-P sites abrogates menin protein expression. Men1$^{f/f}$ cells were either infected with adenovirus Ad-GFP (Men1$^{f/f}$ cell line) or Ad-Cre (Men1$^{\Delta/\Delta1}$ and Men1$^{\Delta/\Delta2}$, two independent pools of the infected cells) before detection of menin and with control actin 5 days after infection. B) excision of Men1 in the Men1$^{\Delta/\Delta1}$ and Men1$^{\Delta/\Delta2}$ cells was confirmed by genotyping using primers P2 and P3 (lane 1) or P1 and P3 (lanes 2 and 3) as described herein. C) deletion of Men1 in MEFs increases cell proliferation. Men1$^{f/f}$, Men1$^{\Delta/\Delta1}$ and Men1$^{\Delta/\Delta2}$ cells were seeded in triplicate on day 0 and counted using a hemocytometer on day 4. Data were derived from the mean of triplicate cultures.

FIG. 7 shows that excision of Men1 acutely accelerates islet cell proliferation. A) 7 and 14 days after tamoxifen treatment, pancreata from mice (four Men1$^{+/+}$;Cre-ER and three Men1$^{1/1}$;Cre-ER mice for day 7; four Men1$^{+/+}$;Cre-ER and four Men1$^{1/1}$;Cre-ER mice for day 14) were processed for BrdUrd staining as described in FIG. 6C to J. B, quantification of pancreatic islets from mice (four Men1$^{+/+}$; Cre-ER and three Men1$^{1/1}$;Cre-ER mice for day 7; four Men1$^{+/+}$;Cre-ER and four Men1$^{1/1}$;Cre-ER mice for day 14) was done as described in FIG. 6B.

FIG. 8 shows results for half year old mice, which were divided into three groups: menin$^{1/1}$, menin$^{+/+}$ Cre$^{+}$, and menin$^{1/1}$Cre$^{+}$. The mice in the last two groups were fed with tamoxifen at 200 ug/gbw/day for 4 days. Menin$^{1/1}$ mice were fed with corn oil as the control. One month after the last dose of tamoxifen or corn oil, multiple low-dose of streptozotocin (40 mg/kg body weight in citrate buffer, pH 4.0) was injected intraperitoneally once a day for 5 consecutive days. Nonfasting blood was collected before STZ injection. Serum glucose was tested for each sample.

FIG. 13 shows that Men1 expression was not changed in high-fat induced obese C57BL/6J mice. C57BL/6J mice of 4-6 week were fed either high fat diet or regular chow for 13 weeks. Body weights were followed weekly on all mice. Glucose tolerance tests were performed at the beginning and during the last week of feeding as described in the material and methods section. A, body weight. B, GTT. C, Men1 mRNA level. D, immunohistologic detection of menin protein level in pancreatic sections from obese and control mice. *, P<0.05; , P<0.01; *, P<0.001.

FIG. 15 shows that excision of floxed Men1 in pancreatic beta cells ameliorates glucose intolerance in obese mice. A to B, Men1$^{l/l}$;PdxlCre-ER and control Men1$^{l/l}$ mice (n=5 to 10 mice per group) were fed high fat diet or normal chow diet for 16 weeks followed by TAM treatment. GTT were determined before (A) and 4 weeks After (B) TAM treatment. Comparison between the two high fat diet groups; *, P<0.05; , P<0.01; *, P<0.001.

DETAILED DESCRIPTION OF THE INVENTION

Figure 2A:
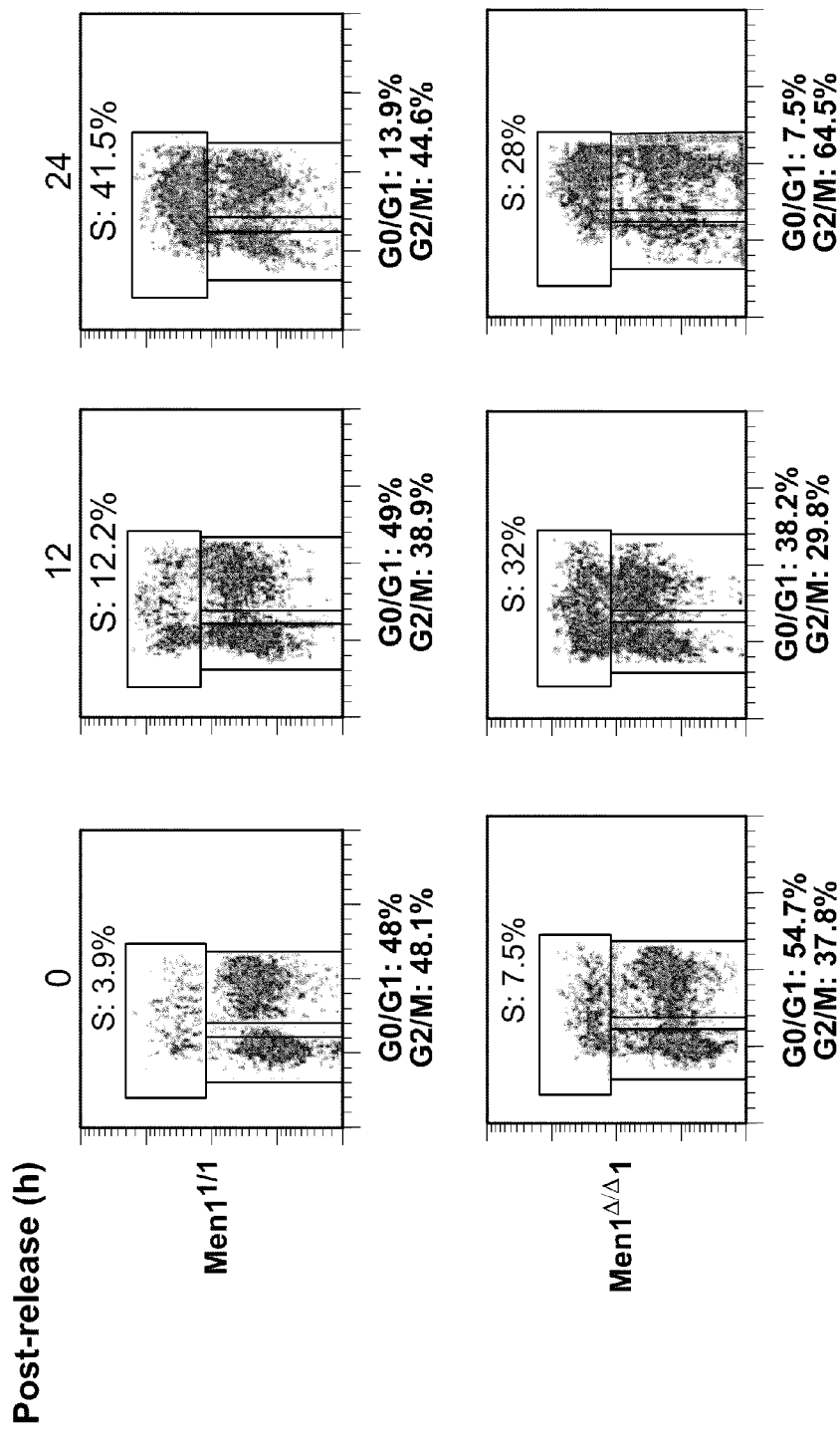
FIG. 2 shows that ablation of Men1 in MEFs accelerates cell cycle progression from G0/G1 to S phase. A) serum-starved Men1$^{f/f}$ and Men1$^{\Delta/\Delta1}$ cells were stimulated with the addition of serum and harvested 0, 6, 12, 18, and 24 hours after release. The cells were pulsed with BrdUrd, harvested, and processed for analysis by flow cytometry. B) detailed kinetics of cell cycle change in G0/G1, S, and G2-M phases in Men1$^{f/f}$ and $^f$ and Men1$^{\Delta/\Delta1}$ cell lines. Duplicate cultures were examined for each time point. Representative of two independent experiments are shown.

This invention relates, in one embodiment, to the inhibition of Men1 expression or function for the purpose of treating diabetes and screening and researching agents capable of inhibiting expression or function of Men1 gene or its encoded proteins for use in treating diabetes. In another embodiment, the disclosed invention shows that inhibition of Men1 expression or function can be employed as a means to specifically stimulate proliferation of islet cells, over 80% of which are insulin-secreting beta cells, to treat diabetes.

In one embodiment, Multiple endocrine neoplasia type 1 (MEN1) refers to a dominantly inherited tumor syndrome that results from the mutation of the tumor suppressor gene Men1, which encodes menin. Menin interacts in another embodiment, with multiple proteins that play critical roles in the regulation of cell proliferation, including JunD, Smad 3, and activator of S-phase kinase. Activator of S-phase kinase is the crucial regulatory factor for protein kinase cdc7 that is required for initiation of DNA replication and menin functionally represses the activity of activator of S-phase kinase. In one embodiment, menin interacts with a protein complex containing the mixed lineage leukemia protein (MLL) and up-regulates transcription of various target genes, including the cyclin-dependent kinase (CDK) inhibitors p27$^{Kip1}$ and p18$^{Ink4c}$ in one embodiment, in transformed fibroblasts and insulinoma cells.

In one embodiment, menin comprises the following amino acid sequence:

(SEQ ID No. 8)
Met-Gly-Leu-Lys-Ala-Ala-Gln-Lys-Thr-Leu-Phe-Pro-Leu-Arg-Ser-Ile-Asp-Asp-Val-Val-Arg-Leu-

-continued

Phe-Ala-Ala-Glu-Leu-Gly-Arg-Glu-Glu-Pro-Asp-Leu-Val-Leu-Leu-Ser-Leu-Val-Leu-Gly-Phe-Val-
Glu-His-Phe-Leu-Ala-Val-Asn-Arg-Val-Ile-Pro-Thr-Asn-Val-Pro-Glu-Leu-Thr-Phe-Gln-Pro-Ser-Pro-
Ala-Pro-Asp-Pro-Pro-Gly-Gly-Leu-Thr-Tyr-Phe-Pro-Val-Ala-Asp-Leu-Ser-Ile-Ile-Ala-Ala-Leu-Tyr-
Ala-Arg-Phe-Thr-Ala-Gln-Ile-Arg-Gly-Ala-Val-Asp-Leu-Ser-Leu-Tyr-Pro-Arg-Glu-Gly-Gly-Val-Ser-
Ser-Arg-Glu-Leu-Val-Lys-Lys-Val-Ser-Asp-Val-Ile-Trp-Asn-Ser-Leu-Ser-Arg-Ser-Tyr-Phe-Lys-Asp-
Arg-Ala-His-Ile-Gln-Ser-Leu-Phe-Ser-Phe-Ile-Thr-Gly-Trp-Ser-Pro-Val-Gly-Thr-Lys-Leu-Asp-Ser-
Ser-Gly-Val-Ala-Phe-Ala-Val-Val-Gly-Ala-Cys-Gln-Ala-Leu-Gly-Leu-Arg-Asp-Val-His-Leu-Ala-
Leu-Ser-Glu-Asp-His-Ala-Trp-Val-Val-Phe-Gly-Pro-Asn-Gly-Glu-Gln-Thr-Ala-Glu-Val-Thr-Trp-
His-Gly-Lys-Gly-Asn-Glu-Asp-Arg-Arg-Gly-Gln-Thr-Val-Asn-Ala-Gly-Val-Ala-Glu-Arg-Ser-Trp-
Leu-Tyr-Leu-Lys-Gly-Ser-Tyr-Met-Arg-Cys-Asp-Arg-Lys-Met-Glu-Val-Ala-Phe-Met-Val-Cys-Ala-
Ile-Asn-Pro-Ser-Ile-Asp-Leu-His-Thr-Asp-Ser-Leu-Glu-Leu-Leu-Gln-Leu-Gln-Gln-Lys-Leu-Leu-Trp-
Leu-Leu-Tyr-Asp-Leu-Gly-His-Leu-Glu-Arg-Tyr-Pro-Met-Ala-Leu-Gly-Asn-Leu-Ala-Asp-Leu-Glu-
Glu-Leu-Glu-Pro-Thr-Pro-Gly-Arg-Pro-Asp-Pro-Leu-Thr-Leu-Tyr-His-Lys-Gly-Ile-Ala-Ser-Ala-Lys-
Thr-Tyr-Tyr-Arg-Asp-Glu-His-Ile-Tyr-Pro-Tyr-Met-Tyr-Leu-Ala-Gly-Tyr-His-Cys-Arg-Asn-Arg-
Asn-Val-Arg-Glu-Ala-Leu-Gln-Ala-Trp-Ala-Asp-Thr-Ala-Thr-Val-Ile-Gln-Asp-Tyr-Asn-Tyr-Cys-
Arg-Glu-Asp-Glu-Glu-Ile-Tyr-Lys-Glu-Phe-Phe-Glu-Val-Ala-Asn-Asp-Val-Ile-Pro-Asn-Leu-Leu-
Lys-Glu-Ala-Ala-Ser-Leu-Leu-Glu-Ala-Gly-Glu-Glu-Arg-Pro-Gly-Glu-Gln-Ser-Gln-Gly-Thr-Gln-
Ser-Gln-Gly-Ser-Ala-Leu-Gln-Asp-Pro-Glu-Cys-Phe-Ala-His-Leu-Leu-Arg-Phe-Tyr-Asp-Gly-Ile-
Cys-Lys-Trp-Glu-Glu-Gly-Ser-Pro-Thr-Pro-Val-Leu-His-Val-Gly-Trp-Ala-Thr-Phe-Leu-Val-Gln-Ser-
Leu-Gly-Arg-Phe-Glu-Gly-Gln-Val-Arg-Gln-Lys-Val-Arg-Ile-Val-Ser-Arg-Glu-Ala-Glu-Ala-Ala-
Glu-Ala-Glu-Glu-Pro-Trp-Gly-Glu-Glu-Ala-Arg-Glu-Gly-Arg-Arg-Arg-Gly-Pro-Arg-Arg-Glu-Ser-
Lys-Pro-Glu-Glu-Pro-Pro-Pro-Lys-Lys-Pro-Ala-Leu-Asp-Lys-Gly-Leu-Gly-Thr-Gly-Gln-Gly-
Ala-Val-Ser-Gly-Pro-Pro-Arg-Lys-Pro-Pro-Gly-Thr-Val-Ala-Gly-Thr-Ala-Arg-Gly-Pro-Glu-Gly-Gly
Ser-Thr-Ala-Gln-Val-Pro-Ala-Pro-Ala-Ala-Ser-Pro-Pro-Pro-Glu-Gly-Pro-Val-Leu-Thr-Phe-Gln-Ser-
Glu-Lys-Met-Lys-Gly-Met-Lys-Glu-Leu-Leu-Val-Ala-Thr-Lys-Jle-Asn-Ser-Ser-Ala-Jle-Lys-Leu-Gln-
Leu-Thr-Ala-Gln-Ser-Gln-Val-Gln-Met-Lys-Lys-Gln-Lys-Val-Ser-Thr-Pro-Ser-Asp-Tyr-Thr-Leu-Ser-
Phe-Leu-Lys-Arg-Gln-Arg-Lys-Gly-Leu.

Figures 3A, 3B:
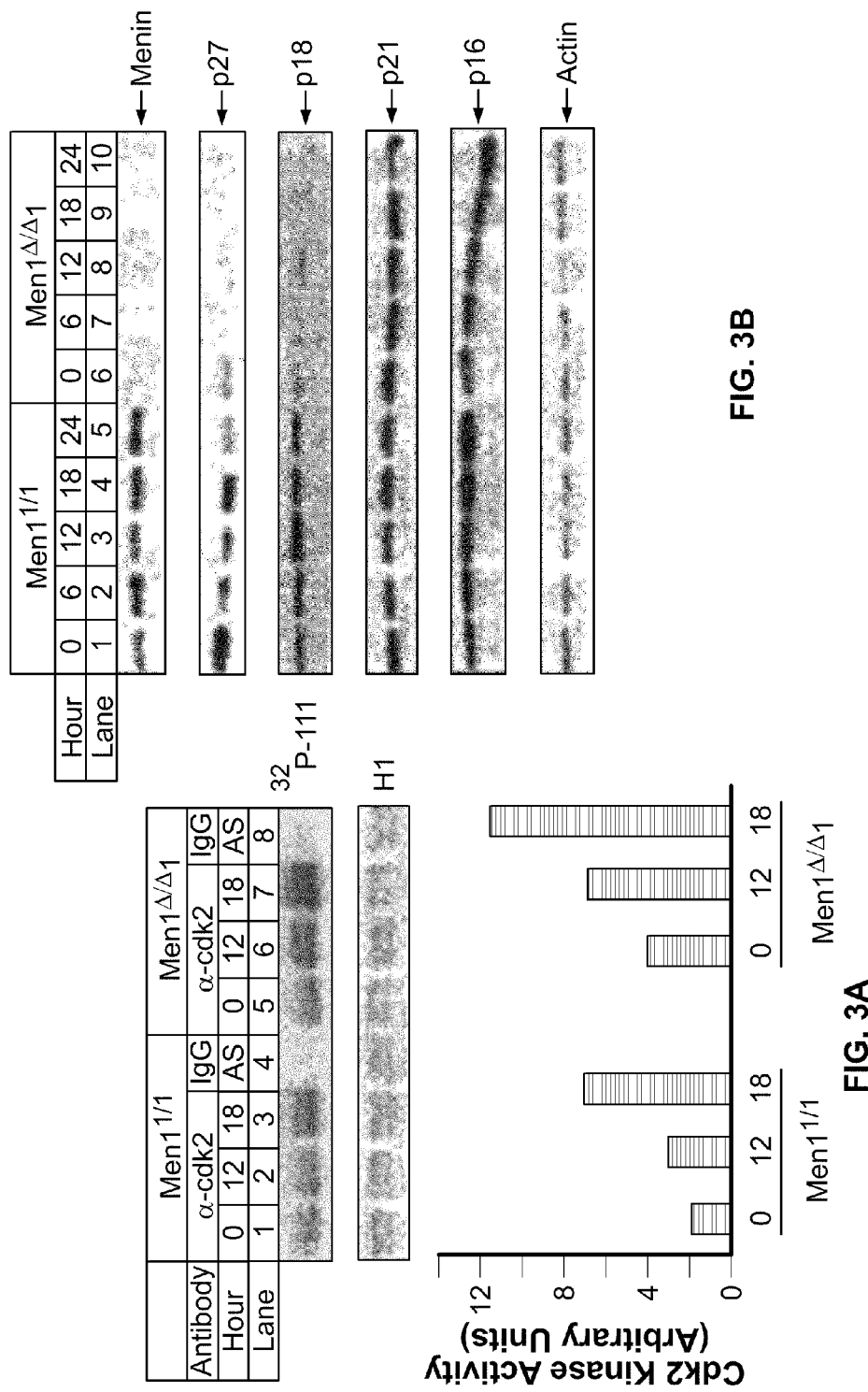
FIG. 3 shows that ablation of Men1 results in increased CDK2 activity and decreased levels of p27$^{Kip1}$ and p18$^{Ink4c}$ protein and RNA. A, ablation of Men1 in MEFs increases CDK2 activity. As in FIG. 2A, serum-starved Men1$^{1/1}$ and Men1$^{\Delta/\Delta1}$ cells were released and harvested for immunoprecipitation with an anti-CDK2 antibody to measure CDK2 activity. B, excision of Men1 in MEFs decreases p18$^{Ink4c}$ and p27$^{Kip1}$ protein levels. The indicated cells were released from serum starvation and harvested at the indicated time points, and then subjected for Western blotting with the indicated antibodies. C, ablation of Men1 decreases p18$^{Ink4c}$ and p27$^{Kip1}$ RNA levels. Real-time TaqMan PCR analysis was carried out using TaqMan probes for p18$^{Ink4c}$, p27$^{Kip1}$, and GAPDH. D, the p27$^{Kip1}$ and p18$^{Ink4c}$ mRNA levels decrease in Men1$^{1/1}$;Cre-ER mice 1 month after tamoxifen treatment as shown by RT-PCR. Representative samples of four mice for each of the genotypes are depicted.

As described herein and in one embodiment, the role of menin in regulating cell cycle progression in vitro was examined and then extended to the proliferation of pancreatic islet cells in vivo. Using MEFs with homozygous conditional Men1 alleles, it is shown, in one embodiment, that Men1 excision accelerates S-phase entry for 4 to 5 hours, providing evidence linking menin to inhibition of cell cycle progression. Accelerated S-phase entry in Men1-excised cells is accompanied, in another embodiment, by decrease of p18$^{Ink4c}$ and p27$^{Kip1}$ in protein levels (FIG. 3B).

In one embodiment, CDK2 plays an important role in G1 to S transition and p18$^{Ink4c}$ and p27$^{Kip1}$ can either directly or indirectly inhibit CDK2. In another embodiment, Men1 excision leads to elevated CDK2 activity, concomitant with down-regulation p18$^{Ink4c}$ and p27$^{Kip1}$ and earlier entry to S phase in MEFs. This is the first time that loss of menin expression is simultaneously linked to down-regulation of p18$^{Ink4c}$ and p27$^{Kip1}$, increased CDK2 activity, and accelerated S-phase entry. In one embodiment, the effect of Men1 excision on cell cycle withdrawal and maintenance of quiescence also contributes in part to the quicker transition to S phase. In another embodiment, menin interacts with and functionally inhibits activator of S-phase kinase, an essential component of protein kinase complex cdc7/activator of S-phase kinase that is required for S-phase entry. Thus, in one embodiment, the menin and activator of S-phase kinase interaction contributes to repression of entry to S-phase.

In one embodiment, a determination of whether deletion of Men1 quickly results in increased islet cell proliferation is made. In one embodiment, within 7 days of Men1 excision, pancreatic islet cells display increased BrdUrd uptake, an indicator of entry into S phase. Consistent with the crucial role of menin in keeping proliferation of islet cells in check and in another embodiment, the mean islet size gradually increases from day 14 to day 30 after Men1 excision. These results establish that, in one embodiment, loss of menin expression acutely results in enhanced cell proliferation in islet cells, a tissue commonly affected in the MEN1 patient. Thus, in another embodiment, menin represses proliferation of islet cells, and an acute and early effect of the Men1 mutation is enhanced proliferation of islet cells including β-cells. In one embodiment defects in genome instability and apoptosis, following Men1 mutation, also contribute to MEN1 tumorigenesis.

Figure 5A:
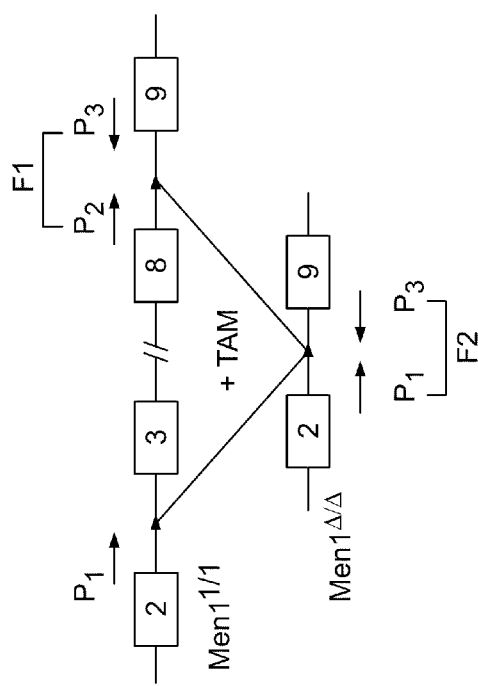
FIGS. 5A and 5B show that tamoxifen effectively induced Men1 expression in the pancreata of the Men1 excision in the pancreata of the Men1$^{1/1}$;Cre-ER mice, but not in Men1$^{+/+}$;Cre-ER mice. The pancreatic sections were stained with anti-menin and anti-BrdUrd antibodies to determine menin expression and the proliferative index of cells. DAPI staining was used to visualize nuclei (E and I). Images were acquired using 20" objective lens. Merged image of (F) and (J) correlates expression of menin (C and G) and the uptake of BrdUrd (D and H). The islet is circled by a dashed line. K) quantification of BrdUrd-positive islet cells from three tamoxifen-treated Men1$^{+/+}$;Cre-ER (control) mice and four Men1$^{1/1}$;Cre-ER mice. L to O) BrdUrd-positive cells express insulin. Pancreatic sections from tamoxifen-fed (1 month after feeding) Men1$^{+/+}$;Cre-ER mice (L) and Men1$^{1/1}$ ;Cre-ER mice (N) were costained with the anti-BrdUrd antibody (red) and the anti-insulin antibody (green). M and o, pancreatic sections were co-stained with the anti-BrdUrd antibody (red) and the anti-glucagon (green) antibody as indicated. Images were captured using 20× objective lens.
Figure 5B:
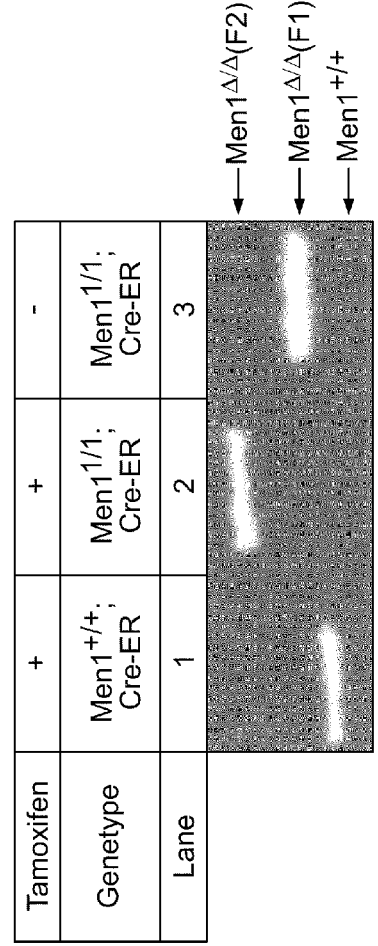
Figure 5L:
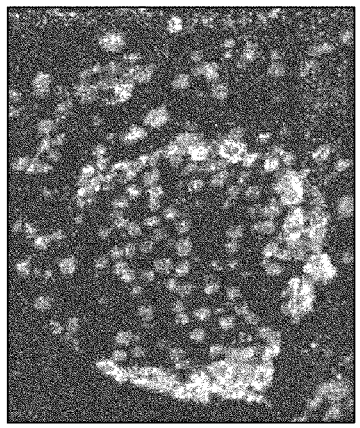
Figure 5M:
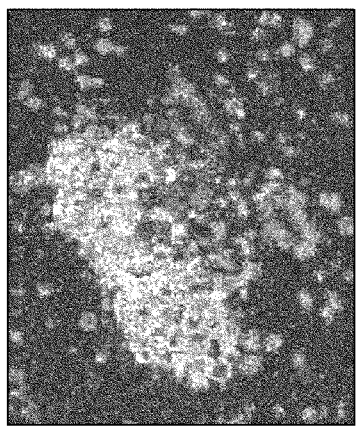

In one embodiment, excision of Men1 accelerates proliferation of islet cells, but not the adjacent exocrine cells, indicating a tissue-specific role for menin in regulating proliferation of the endocrine pancreata. In another embodiment, the floxed Men1 was effectively excised in the pancreas including both the exocrine and endocrine cells, based on analysis of the genomic DNA for the floxed Men1 (FIG. 5B). In another embodiment, the floxed Men1 locus was also effectively excised from other tissues such as bone marrow and the mouse tail. This is consistent with the expected broad expression of the Cre-ER transgene. In one embodiment, inactivation of Men1 in the liver, a tissue not affected in MEN1 syndrome, does not result in tumorigenesis. Thus, in one embodiment, menin plays an especially critical role in suppressing cell proliferation in endocrine organs.

In one embodiment, menin normally regulates the levels of $p18^{Ink4c}$ and $p27^{Kip1}$ to repress CDK2 activity and limit islet cell proliferation. Accordingly, mutation of Men1 results in increased islet cell proliferation. In another embodiment, Men1 excision quickly results in increased pancreatic islet proliferation, which helps to initiate development of islet hyperplasia. In one embodiment, enhanced proliferation of pancreatic islet cells, in combination with decreased apoptosis and genome stability in another embodiment, further accelerates the rate of secondary genetic and/or epigenetic alterations, leading to the development of islet hyperplasia. In another embodiment, additional menin-related regulators, such as JunD, cyclin D1, and activator of S-phase kinase, may also be involved in the regulation of islet cell proliferation. In one embodiment, menin plays an essential role in the tissue-specific suppression of pancreatic islet cell proliferation and in inhibition of the G0/G1-S-transition. In another embodiment, targeting the CDK2 axis is useful in treating MEN1 islet tumors. In another embodiment, menin interacts with mixed lineage leukemia (MLL) protein, a histone methyltransferase that is involved in upregulating $p27^{abd}$ p18 and repression of cell proliferation, such that in one embodiment, menin inhibits beta cell proliferation through interacting with MLL and upregulating p27 and p18, both inhibitors of cyclin-dependent kinases (CDKs).

Therefore, according to this aspect of the invention and in one embodiment, the invention provides a method of treating diabetes either type I or type II, in a subject, comprising the step of contacting a pancreatic cell of said subject with an effective amount of an agent capable of inhibiting the expression or function of Men1 gene or its encoded proteins, whereby the inhibition of expression or function of Men1 gene or its encoded proteins results in increasing insulin production in said pancreatic cell, thereby reducing blood sugar level.

In one embodiment, the term "treatment", or "treating" refers to any process, action, application, therapy, or the like, wherein a subject, including a human being, is subjected to medical aid with the object of improving the subject's condition, directly or indirectly. The term "treating" refers also to reducing incidence, or alleviating symptoms, eliminating recurrence, preventing recurrence, preventing incidence, improving symptoms, improving prognosis or combination thereof in other embodiments.

In another embodiment, "treating" comprises reducing incidence, inhibiting or suppressing, whereby inhibiting the expression or function of Men1 gene or its encoded proteins, by the agents used in the methods and compositions described herein, for the treatment of diabetes, comprises lowering the level of a protein or nucleic acid regulating the expression or function of said Men1 gene, or inhibiting function of Men1 gene's encoded proteins. In one embodiment, the agent used in the compositions and methods described herein, is a siRNA, polyamides, triple-helix-forming agents, antisense RNA, synthetic peptide nucleic acids (PNAs), agRNA, LNA/DNA copolymers, small molecule chemical compounds, or a combination thereof.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. Therefore, in one embodiment, the invention provides a method of treating diabetes, of either type I or type II, in a diabetic human subject, comprising the step of contacting a pancreatic cell of said subject with an effective amount of an agent capable of inhibiting the expression or function of Men1 gene or its encoded proteins, whereby the inhibition of expression or function of Men1 gene or its encoded proteins results in increasing insulin production in said pancreatic cell, thereby reducing blood sugar level.

In one embodiment, the method of treating a high fat diet associated diabetes, in a subject, comprises the step of administering said subject with an effective amount of an agent capable of inhibiting the expression or function of Men1 gene or its encoded proteins, whereby the inhibition of expression or function of Men1 gene or its encoded proteins results in increasing insulin production in said subject's pancreatic cells, thereby reducing blood sugar level. In another embodiment, the method of treating an obesity associated diabetes, in a subject, comprises the step of administering said subject with an effective amount of an agent capable of inhibiting the expression or function of Men1 gene or its encoded proteins, whereby the inhibition of expression or function of Men1 gene or its encoded proteins results in increasing insulin production in said subject's pancreatic cells, thereby reducing blood sugar level.

In another embodiment, the diabetes treated by the methods and compositions described herein, is associated with the combinations of high fat diet and obesity. In another embodiment, the diabetes treated by the methods and compositions described herein, is associated with high hyperglycemia, or glucose intolerance, or their combinations in other discrete embodiments. In another embodiment, the diabetes treated by the methods and compositions described herein, is a Type 2 diabetes. In yet another embodiment, the diabetes treated by the methods and compositions described herein, is a Type 1 diabetes. In further embodiment, the diabetes treated by the methods and compositions described herein, is a pre-diabetes. In a particular embodiment, the diabetes treated by the methods and compositions described herein, is a gestational diabetes.

In one embodiment the terms "obesity" and "obese" refers to an excess of adipose tissue. In this context obesity is best viewed as any degree of excess adiposity that imparts a health risk. The distinction between normal and obese individuals can only be approximated, but the health risk imparted by obesity is probably a continuum with increasing adiposity. However, in the context of the present invention, human individuals with a body mass index (BMI=body weight in kilograms divided by the square of the height in meters) above 25 are to be regarded as obese.

In another embodiment, the term "High-fat (HF) diet" refers to that given by M. R. Freedman et al. in a review article in Obesity Research 9, Suppl. 1 (March 2001) pp. 1S 40S, incorporated herein by reference.

In one embodiment, the term "siRNA" refers to RNA interference, which in another embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved in one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

In one embodiment, the term "conserved", refers to amino acid sequences comprising the peptides or nucleotides described herein, which remain in one embodiment, essentially unchanged throughout evolution, and exhibit homology among various species producing the protein.

The presence of long dsRNAs in cells stimulates, in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression, which, in another embodiment is the Men1 gene encoding the menin protein described herein. In one embodiment, the agent used for reducing the level or function of Men1 gene or its encoded protein, is a siRNA specific for the nucleic acid encoding Men1.

In one embodiment, the siRNA of the Men1 gene encoding the menin protein described herein exhibits substantial complementarity to its target sequence. In another embodiment, "complementarity" indicates that the oligonucleotide has a base sequence containing an at least 15 contiguous base region that is at least 70% complementary, or in another embodiment at least 75% complementary, or in another embodiment at least 80% complementary, or in another embodiment at least 85% complementary, or in another embodiment at least 90% complementary, or in another embodiment at least 95% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of the Men1 gene encoding the menin protein described herein is sufficiently complimentary to its target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, minor groove-binding N-methylpyrrole (Py) and N-methylimidazole (Im) polyamides (peptides) uniquely recognize each of the four Watson-Crick base pairs. Antiparallel pairing of imidazole with pyrrole (Im/Py) recognizes in opne embodiment, a G-C base pair, whereas in another embodiment, a Py/Py pair recognizes either an A-T or T-A base pair. The binding constant and sequence-specificity of the Py-Im hairpin polyamides are similar to that of a transcription factor. Therefore, many genes are silenced, in other embodiments, by competitive binding of Py-Im hairpin polyamides to their regulatory sequences. Gene expression is controlled in one embodiment, by a combination of multiple common transcription factors. In one embodiment, inhibition of gene expression through the binding of Py-Im polyamides to regulatory sequences is unique to a specific gene, and contains part of the recognition sequence of the transcription factor together with the unique flanking sequences. In another embodiment, targeting Py-Im polyamide to the coding region is more straightforward when selecting a unique sequence. In one embodiment, the agent used to silence the Men1 gene in the methods and compositions described herein, is Py-Im polyamide specific for the coding region of Men1, or to regulatory sequences is unique to Men1 in another embodiment. In another embodiment, the agent used to silence the Men1 gene in the methods and compositions described herein, is a synthetic polyamide nucleic acid (PNA) specific for the coding region of Men1, or to regulatory sequences is unique to Men1 in another embodiment.

In one embodiment, the polyamides used in the compositions and methods described herein, which, in another embodiment are referred to as "peptide nucleic acid" (PNA) or "synthetic peptide nucleic acids", are alkylating Py-Im polyamides that show sequence-specific DNA alkylation. In another embodiment, alkylation of a template strand in the coding region of Men1, by Py-Im polyamide-cyclopropylpyrroloindole (CPI) conjugates with a vinyl linker results in the production of truncated mRNA, effectively inhibiting transcription of Men1 in vitro. In one embodiment, Py-Im tetra-hydro-cyclo-propabenzindolone (CBI) conjugates with indole linkers are the alkylating polyamides used as the agent capable of inhibiting the expression or function of Men1 gene, because indole-CBI has increased chemical stability under acidic and basic conditions.

In another embodiment, oligodeoxynucleotides utilized in methods and compositions described herein inhibit cellular transcription by binding to duplex DNA to form a triple helix. Due to the possibility of long-term inhibition of the gene product, oligodeoxynucleotides that can bind duplex DNA have advantages over those that bind mRNA or proteins. These oligodeoxynucleotides are generally called triplex forming oligonucleotides (TFOs). By using DNA-specific TFOs, the inhibition of expression of several cellular genes has been demonstrated, including the oncogene, c-myc, the human immunodeficiency virus-1, the alpha chain of the interleukin 2 receptor, the epidermal growth factor receptor, the progesterone responsive gene and the mouse insulin receptor. In one embodiment, the oligonucleotides used in the methods and compositions described herein, can bind to duplex DNA and form triple helices in a sequence-specific manner and will silence expression or function of Men1.

In one embodiment, homopyrimidine DNA strand (triplex forming oligonucleotide, TFO) can bind to a homopurine/homopyrimide DNA duplex in the major groove by forming Hoogsteen base pairs with the homopurine strand. The Hoogsteen base pairing scheme mediates sequence specific recognition of the double stranded DNA by the TFO where in one embodiment, an AT base pair is recognized by a T; and a GC base pair by a C that is protonated at $N3^+$. In another embodiment, homopurine strands specifically form a DNA triplex in which the AT base pair is contacted by an A; and the GC base pair by a G. In one embodiment, the agent capable of inhibiting the expression or function of Men1 gene is a triple-helix-forming agents. In another embodiment, the triple-helix-forming agents are olygonucletides. In one embodiment, oligonucleotide-mediated triplex formation prevent transcription factor binding to promoter sites and block mRNA synthesis in vitro and in vivo. In another embodiment, DNA intercalating or cross-linking agents are used to prolong oligonucleotide-duplex interactions.

In one embodiment, the term "TFO" or "triplex forming oligonucleotide" refers to the synthetic oligonucleotides of the present invention which are capable of forming a triple helix by binding in the major groove with a duplex DNA structure.

In another embodiment, the term "bases" refers to both the deoxyribonucleic acids and ribonucleic acids. The following abbreviations are used, "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods described herein, without changing the scope of the invention.

The term "nucleic acid" as used in connection with siRNA, refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nucleic acid sequences.

In one embodiment oligomeric antisense compounds, particularly oligonucleotides, are used in modulating the function of nucleic acid molecules encoding Men1, ultimately modulating the amount of menin produced. This is accomplished by providing antisense compounds which specifically hybridize with one or more nucleic acids encoding Men1. As used herein, the terms "target nucleic acid" and "nucleic acid encoding Men1" encompass DNA encoding Men1, RNA (including pre-mRNA and mRNA) transcribed from such DNA, and also cDNA derived from such RNA. The specific hybridization of an oligomeric compound with its target nucleic acid interferes in another embodiment, with the normal function of the nucleic acid. The modulation of function of a target nucleic acid by compounds which specifically hybridize to it, is referred to in one embodiment as "antisense". In one embodiment, the functions of DNA to be interfered with using the antisense oligonucleotides described herein, which are used in the methods and compositions described herein, include replication and transcription. In another embodiment, functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Men1. In one embodiment, inhibition of gene expression is preferred and mRNA is a preferred target. In one embodiment, since many genes (including Men1) have multiple transcripts, "inhibition" also includes an alteration in the ratio between gene products, such as alteration of mRNA splice products.

In one embodiment, specific nucleic acids are targeted for antisense. "Targeting" an antisense compound to a particular nucleic acid, in one embodiment, is a multistep process. The process usually begins with the identification of a nucleic acid sequence whose function is to be inhibited. This may be, for example, a cellular gene (or mRNA transcribed from the gene) whose expression is associated with a particular disorder or disease state, or a nucleic acid molecule from an infectious agent. In one embodiment, the target is a nucleic acid molecule encoding Men1. The targeting process also includes in another embodiment, determination of a site or sites within this gene for the antisense interaction to occur such that the desired effect, e.g., inhibition of expression of the protein such as menin, will result. In one embodiment, an intragenic site is the region encompassing the translation initiation or termination codon of the open reading frame (ORF) of the gene. Since, the translation initiation codon is in one embodiment 5'-AUG (in transcribed mRNA molecules; 5'-ATG in the corresponding DNA molecule), the translation initiation codon is referred to in one embodiment as the "AUG codon," the "start codon" or the "AUG start codon". In another embodiment, a minority of genes have a translation initiation codon having the RNA sequence 5'-GUG, 5'-UUG or 5'-CUG, and 5'-AUA, 5'-ACG and 5'-CUG and have been shown to function in vivo. Thus, the terms "translation initiation codon" and "start codon" encompasses in other embodiments, many codon sequences, even though the initiator amino acid in each instance is typically methionine (in eukaryotes) or formylmethionine (in prokaryotes). In another embodiment, "start codon" and "translation initiation codon" refer to the codon or codons that are used in vivo to initiate translation of an mRNA molecule transcribed from a gene encoding Men1, regardless of the sequence(s) of such codons.

In certain embodiments, a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer in one embodiment, to a portion of such a mRNA or gene that encompasses from about 25 to about 50 contiguous nucleotides in either direction (i.e., 5' or 3') from a translation initiation codon. In another embodiment, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," refers in one embodiment to the region between the translation initiation codon and the translation termination codon, is a region which may be targeted effectively. Other target regions include in other embodiments, the 5' untranslated region (5'UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises in one embodiment, an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region is a preferred target region in one embodiment.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be target regions in one embodiment, and are particularly useful in situations where aberrant splicing is implicated in disease, or where an overproduction of a particular mRNA splice product is implicated in disease in other embodiment, such as diabetes or MEN1 syndrome. Aberrant fusion junctions due to rearrangements or deletions are also preferred targets. In one embodiment, introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect. In one embodiment, the term "hybridization" refers to hydrogen bonding, which may be Watson-Crick, Hoogsteen or reversed Hoogsteen hydrogen bonding, between complementary nucleoside or nucleotide bases. In one embodiment, adenine and thymine are complementary nucleotide bases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are used in one embodiment, as research reagents and diagnostics. In another embodiment, antisense oligonucleotides, which are able to inhibit gene expression, such as the Men1 gene, with extreme specificity, are used by those of ordinary skill to elucidate the function of particular genes. Antisense compounds are used in another embodiment, to distinguish between functions of various members of a biological pathway. Antisense modulation has, in one embodiment of the agents described in the methods and compositions described herein, been harnessed for research use.

In one embodiment, the specificity and sensitivity of antisense agents described herein, is also harnessed for therapeutic uses. Antisense oligonucleotides are employed in one embodiment, as therapeutic moieties in the treatment of disease states in animals and man. In one embodiment, antisense oligonucleotides are safely and effectively administered to humans. In one embodiment oligonucleotides are useful therapeutic modalities that can be configured to be useful in treatment regimes of cells, tissues and animals, especially humans. In one embodiment, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In one embodiment, the oligonucleotides used in the methods and compositions described herein, are synthetic peptide nucleic acids (PNAs) which interact with the nucleotide sequence encoding Men1 in a sequence-specific manner and silence expression or function of Men1. In another embodiment, the oligonucleotides used in the methods and compositions described herein, are locked nucleic acid (LNA), which interact with the nucleotide sequence encoding Men1 forming a LNA/DNA co-polymer, in a sequence-specific manner and substantially silence expression or function of Men1.

In one embodiment, the term "locked nucleic acid" (LNA) refers to a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. In one embodiment, LNA can be joined to DNA molecules by conventional techniques. Therefore, in one embodiment, LNA is to be preferred over PNA, for use in the agents of the methods and compositions described herein.

In one embodiment, the target specific regions of the agent that is able to inhibit gene expression, such as the Men1 gene, may comprise LNA and/or PNA and the arm region comprise DNA, with the agent further comprising a destabilizing moiety.

In another embodiment, the agent capable of inhibiting expression or function of Men1 gene, or its encoded protein is an agPNA. In another embodiment, this antibody is referred to as antigenic PNA.

Polypeptides of the invention or a fragment thereof may be used to produce antibodies specifically reactive with the polypeptide. For example, a recombinant Men1 polypeptide or an antigenic fragment thereof, may be isolated. Recombinant protein is a useful immunogen for the production of monoclonal or polyclonal antibodies. Alternatively, a synthetic peptide derived from Men1 polypeptide sequences and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein. Once specific antibodies are available, binding interactions with the Men1 polypeptide can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane).

In another embodiment, the method of treating diabetes of the invention comprises the step of enhancing glucose-sensing. In another embodiment, the method comprises the step of administering to a subject with an effective amount of an agent capable of inhibiting the expression or function of a Men1 gene or a protein encoded thereby, whereby the inhibition of expression or function of said Men1 gene or said protein enhances glucose-sensing in said subject. In another embodiment, the method enhances glucose-sensing via increased expression of GLUT. In another embodiment, the method enhances glucose-sensing via increased expression of GK. In yet another embodiment, the method enhances glucose-sensing via increased expression of GLUT and GK.

In one embodiment, the agents described hereinabove are used in the compositions described herein.

In another embodiment, the invention provides a composition for the treatment diabetes in a subject, comprising an effective amount of an agent capable of inhibiting the expression or function of Men1 gene of said subject, resulting in selective proliferation of pancreatic cells. In another embodiment, the diabetes treated with the methods and compositions described herein, is a type I diabetes. In another embodiment, the diabetes is a type II diabetes.

In one embodiment, the compositions of the invention are administered in conjunction with other therapeutic agents. Representative agents that can be used in combination with the compositions of the invention are agents used to treat diabetes such as insulin and insulin analogs (e.g. LysPro insulin); GLP-1 (7-37) (insulinotropin) and GLP-1 (7-36)—NH.sub.2; biguanides: metformin, phenformin, buformin; .alpha.2-antagonists and imidazolines: midaglizole, isaglidole, deriglidole, idazoxan, efaroxan, fluparoxan; sulfonylureas and analogs: chlorpropamide, glibenclamide, tolbutamide, tolazamide, acetohexamide, glypizide, glimepiride, repaglinide, meglitinide; other insulin secretagogues: linogliride, A-4166; glitazones: ciglitazone, pioglitazone, englitazone, troglitazone, darglitazone, rosiglitazone; PPAR-gamma agonists; fatty acid oxidation inhibitors: clomoxir, etomoxir; .alpha.-glucosidase inhibitors: acarbose, miglitol, emiglitate, voglibose, MDL-25,637, camiglibose, MDL-73, 945, .beta.-agonists: BRL 35135, BRL 37344, Ro 16-8714, ICI D7114, CL 316,243; phosphodiesterase inhibitors: L-386,398; lipid-lowering agents: benfluorex; antiobesity agents: fenfluramine; vanadate and vanadium complexes (e.g. Naglivan.RTM.)) and peroxovanadium complexes; amylin antagonists; glucagon antagonists; gluconeogenesis inhibitors; somatostatin analogs and antagonists; antilipolytic agents: nicotinic acid, acipimox, WAG 994. Also contemplated for use in combination with the compositions of the invention are pramlintide acetate (Symlin™.), AC2993, glycogen phosphorylase inhibitor and nateglinide. Any combination of agents can be administered as described hereinabove. In one embodiment, dipeptidypeptidase-4 (DPP-4) inhibitors; vildagliptin (LAF 237), sitagliptin (MK 0431), ZP10, or combination thereof are given with the compositions and methods of the invention as oral antidiabetic medication as well.

Type I diabetes begins, in one embodiment, before the clinical manifestations of the disease. It starts with the progressive destruction of β-cells in the pancreas. These cells normally produce insulin. The reduction of insulin response to glucose can be measured during this period, however. Ultimately, there is massive (>90%) destruction of β-cells in the islets of Langerhans. During the early stages of the disease and beyond, type I diabetes is characterized by the infiltration of pancreatic islets by macrophages and lymphocytes (helper and killer). The macrophage infiltration prompts, in another embodiment, the infiltration of small lymphocytes. In one embodiment, as described in example 4; Men1 excision in pancreatic islets acutely results in increased islet cell proliferation and size, thereby being a method for treating type I diabetes.

Type II diabetes is characterized, in another embodiment, by insulin and resistance, i.e., a failure of the normal metabolic response of peripheral tissues to the action of insulin. In one embodiment, insulin resistance refers to a condition where the circulating insulin produces a subnormal biological response. In clinical terms, insulin resistance is present when normal or elevated blood glucose levels persist in the face of normal or elevated levels of insulin. The hyperglycemia associated with Type II diabetes is reversed or ameliorated in one embodiment by diet or weight loss sufficient to restore the sensitivity of the peripheral tissues to insulin. In another embodiment, type II diabetes mellitus is characterized by hyperglycemia in the presence of higher than normal levels of plasma insulin. Progression of Type II diabetes mellitus is associated in one embodiment, with increasing concentrations of blood glucose and coupled with a relative decrease in the rate of glucose-induced insulin secretion. Thus, in another embodiment, in early (late)-stage Type II diabetes mellitus, an insulin deficiency persists. In one embodiment, Men1-excised mice treated with strepzotocin (mimicking type I diabetes) exhibit normal serum glucose levels (see FIGS. 9 and 10) indicating that in another embodiment, preventing or suppressing the expression of Men1 or its encoded protein, or their function, may be used in the treatment of DM types I & II.

In one embodiment, the diabetic patient is in early stage of Type 2 diabetes, wherein the number of β-cells are insufficient to secrete enough insulin, whereby inhibition of menin using the compositions and methods described herein, increases number of β-cells, their mass and secretion of insulin, thus lowering blood sugar. In another embodiment, inhibition of menin pathway through the inhibition of expression or function of Men1 gene benefits both Type 1 and Type 2 diabetic patients at certain stages.

In one embodiment, the diabetic patient is in early stage of type I diabetes wherein there remain certain number of viable β cells, and inhibition of menin using the compositions and methods described herein, accelerates in one embodiment the proliferation of these cells, increasing β cell mass and ameliorate blood sugar levels. In one embodiment, the diabetic patient is in early stage of type II diabetes, wherein the number of β-cells are insufficient to secrete enough insulin, whereby inhibition of menin using the compositions and methods described herein, increases β-cell mass and secretion of insulin, thus lowering blood sugar. In another embodiment, inhibition of menin pathway through the inhibition of expression or function of Men1 gene benefits both type I and type II diabetic patients at certain stages.

In another embodiment, the invention provides a pancreatic stem cell for treating a Type 2 diabetes in a subject, comprising an agent capable of inhibiting the expression or function of a Men1 gene or a protein encoded thereby, whereby the inhibition of expression or function of said Men1 gene or said protein results in reducing blood sugar level of said subject. The pancreatic stem cell, according to another embodiment, is a transplantable pancreatic stem cell. In another embodiment, the transplantable pancreatic stem cell comprising the agent is transplanted to a subject in accordance with a method known to one of skill in the art (See e.g., *Nature Medicine,* 2000 (6):278-82; *Drug Discov Today* 2008 (19-20): 888-93).

In one embodiment, the compositions described herein are used in the methods described herein. In one embodiment, the invention provides a method of increasing proliferation of pancreatic β-cells in a subject, comprising the step of inhibiting expression or function of Men1 gene in the pancreas of said subject. In one embodiment, Men1$^{\Delta/\Delta}$1 cells enter S phase (FIG. 2A, bottom middle) at a shorter time frame whereas cells containing Men1$^{\Delta/\Delta 1}$ were in S phase, as they had already passed their peak at S phase (18 hours) and progressed to G2-M (FIG. 2A, bottom right). In one embodiment, inhibiting expression or function of Men1 gene in the pancreas of said subject comprises contacting the pancreas of said subject with a therapeutically effective amount of an agent capable of inhibiting the expression or function of said Men1 gene. In one embodiment, Men1 excision leads to increased proliferation of islet cells well before the development of islet cell hyperplasia.

In another embodiment, the invention provides a pharmaceutical composition for the treatment of a high fat diet associated diabetes in a subject, comprising an effective amount of an agent capable of inhibiting the expression or function of Men1 gene of said subject, resulting in selective proliferation of pancreatic cells. In another embodiment, the invention provides a pharmaceutical composition for the treatment of an obesity associated diabetes in a subject, comprising an effective amount of an agent capable of inhibiting the expression or function of Men1 gene of said subject, resulting in selective proliferation of pancreatic cells. In an exemplary embodiment, the diabetes treated with the methods and compositions described herein, is a Type 2 diabetes.

In another embodiment, provided herein is a method of reducing blood sugar in a diabetic subject, comprising the step of administering to the subject an agent capable of inhibiting the expression or function of Men1 gene or its encoded proteins in pancreatic cells, thereby resulting in reduction of blood sugar in the diabetic subject. In another embodiment, inhibition of a single protein, such as menin in one embodiment, can correct the high blood glucose levels in a diabetic subject.

In one embodiment, administering to the subject an agent that induces β-cell regeneration by targeting the menin pathway. Such a treatment abrogates in one embodiment, or diminishes in another embodiment, the need for insulin injections or β-cell transplantation. In another embodiment, the methods and compositions provided herein are useful for patients with either type 1 or type 2 diabetes, thereby capable of benefiting millions of patients.

In one embodiment, the invention provides a method of screening for therapeutic agents for the treatment of diabetes in a subject, comprising the step of: contacting a pancreatic cell of said subject with the candidate therapeutic agent; and analyzing for the expression or function of Men1 gene in said contacted cell, wherein inhibition of the expression or function of Men1 gene in said pancreatic cell indicates the candidate therapeutic agent is effective in treating diabetes. In another embodiment, screening is carried out ex-vivo, or in another embodiment in-vivo.

In one embodiment, the invention provides a method of screening for therapeutic agents for the treatment of high-fat diet associated diabetes in a subject, comprising the step of: contacting a pancreatic cell of said subject with the candidate therapeutic agent; and analyzing for the expression or function of Men1 gene in said contacted cell, wherein inhibition of the expression or function of Men1 gene in said pancreatic cell indicates the candidate therapeutic agent is effective in treating diabetes. In another embodiment, the invention provides a method of screening for therapeutic agents for the treatment of an obesity associated diabetes in a subject, comprising the step of: contacting a pancreatic cell of said subject with the candidate therapeutic agent; and analyzing for the expression or function of Men1 gene in said contacted cell, wherein inhibition of the expression or function of Men1 gene in said pancreatic cell indicates the candidate therapeutic agent is effective in treating diabetes. In another embodiment, screening is carried out ex-vivo, or in another embodiment in-vivo.

In one embodiment, screening encompasses small molecules as well as compounds affecting binding partner proteins for menin. As used herein, the term "binding partner" refers to a polypeptide or other agent that binds to (associates with) a protein according to the invention. Exemplary binding partners are described below; however, the term includes in certain embodiments ligands such as antibodies and other polypeptides capable of binding to proteins, chemical ligands, nucleic acid ligands such as RNA aptamers and natural ligands such as those normally associated with the protein. As used herein, the term "associates" or "binds" refers to binding partners as described herein having a binding constant sufficiently strong to allow detection of binding to the protein by a detection means. In one embodiment, the binding partner is Smad3, a downstream component of the TGF-β signaling pathway. In another embodiment, binding partner is TGF-β.

A number of different screening protocols can be utilized to identify agents that modulate the level of expression or activity of an Men1 polynucleotide or Men1 polypeptide of the invention. In some embodiments, such assays are performed on cells, particularly mammalian cells, and especially human cells. In general terms, the screening methods involve screening a plurality of agents to identify an agent that modulates the activity of a polypeptide of the invention by, e.g., binding to the polypeptide, preventing an activator from binding to the polypeptide, increasing association of an inhibitor with the polypeptide, or inhibiting expression of the polypeptide or mRNA encoding Men1. Any cell expressing a full-length Men1 polypeptide or an active fragment or variant thereof can be used to identify modulators. In some embodiments, the cells are eukaryotic cells lines transformed to express a heterologous Men1 polypeptide. Agents that are initially identified by any of the foregoing screening methods can be further tested to validate the activity. In some embodiments, the Men1 inhibitors are tested for their ability to reduce or inhibit diabetes. Validity of the inhibitors, for example, can also be tested in suitable animal models. The basic format of such methods involves administering a lead compound identified during an initial screen to an animal that serves as a model for human disease (e.g., Type 2 diabetes) and/or determining if expression or activity of a polypeptide or polynucleotide of interest is in fact modulated.

In one embodiment, the compositions of the invention are administered in conjunction with other therapeutic agents. Representative agents that can be used in combination with the compositions of the invention are agents used to treat diabetes such as insulin and insulin analogs (e.g. LysPro insulin); GLP-1 (7-37) (insulinotropin) and GLP-1 (7-36)—NH.sub.2; biguanides: metformin, phenformin, buformin; .alpha.2-antagonists and imidazolines: midaglizole, isaglidole, deriglidole, idazoxan, efaroxan, fluparoxan; sulfonylureas and analogs: chlorpropamide, glibenclamide, tolbutamide, tolazamide, acetohexamide, glypizide, glimepiride, repaglinide, meglitinide; other insulin secretagogues: linogliride, A-4166; glitazones: ciglitazone, pioglitazone, englitazone, troglitazone, darglitazone, rosiglitazone; PPAR-gamma agonists; fatty acid oxidation inhibitors: clomoxir, etomoxir; .alpha.-glucosidase inhibitors: acarbose, miglitol, emiglitate, voglibose, MDL-25,637, camiglibose, MDL-73, 945, .beta.-agonists: BRL 35135, BRL 37344, Ro 16-8714, ICI D7114, CL 316,243; phosphodiesterase inhibitors: L-386,398; lipid-lowering agents: benfluorex; antiobesity agents: fenfluramine; vanadate and vanadium complexes (e.g. Naglivan.RTM.)) and peroxovanadium complexes; amylin antagonists; glucagon antagonists; gluconeogenesis inhibitors; somatostatin analogs and antagonists; antilipolytic agents: nicotinic acid, acipimox, WAG 994. Also contemplated for use in combination with the compositions of the invention are pramlintide acetate (Symlin™), AC2993, glycogen phosphorylase inhibitor and nateglinide. Any combination of agents can be administered as described hereinabove. In one embodiment, dipeptidypeptidase-4 (DPP-4) inhibitors; vildagliptin (LAF 237), sitagliptin (MK 0431), ZP10, or combination thereof are given with the compositions and methods of the invention as oral antidiabetic medication as well.

Compositions of the invention can be administered directly to a mammalian subject (e.g., a human) using any route known in the art, including e.g., by injection (e.g., intravenous, intraperitoneal, subcutaneous, intramuscular), inhalation, transdermal application, rectal administration, or oral administration.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time, e.g., at least a reduction of prostate or breast cancer cell growth, proliferation or metastasis. The optimal dose level for any patient will depend on a variety of factors including the efficacy of the specific modulator employed, the age, body weight, physical activity, and diet of the patient, on a possible combination with other drugs, and on the cancer. The size of the dose also will be determined by the existence, nature, and extent of any adverse side-effects that accompany the administration of a particular compound or vector in a particular subject.

In one embodiment, menin interacts with mixed lineage leukemia (MLL) protein, a histone methyltransferase that is involved in upregulating $p27^{kip1}$, $p18^{Ink4c}$, or both and repression of cell proliferation. In another embodiment menin inhibits beta cell proliferation through interacting with MLL and upregulating of p27 and p18, both inhibitors of cyclin-dependent kinases (CDKs). In another embodiment the binding partner for menin as described herein, is MLL protein, or histone methyltransferase, or their combination in other embodiments.

In one embodiment, cell cycle progression is controlled by the periodic activation of cyclin-dependent kinases (cdks). Cdks become activated by their association with activating subunits, referred to as cyclins. The cdk4/cyclin-D complexes function in the early G1 phase of the cell cycle, whereas cdk2/cyclin-E complex is activated later in the G1 phase. In one embodiment, menin which is encoded by the Men1 gene interacts with a protein complex containing the mixed lineage leukemia protein and up-regulates transcription of various target genes, including the cyclin-dependent kinase (CDK) inhibitors $p27^{Kip1}$ and $p18^{Ink4c}$, in transformed fibroblasts and insulinoma cells. In another embodiment, simultaneous loss of $p27^{Kip1}$ and $p18^{Ink4c}$ produce a spectrum of endocrine tumors similar to that seen in human MEN1 syndrome, including tumors in the pituitary, parathyroid, thyroid, endocrine pancreas, stomach, and duodenum.

In one embodiment, the invention provides a method of inducing CDK2 activity, in a cell comprising the step of contacting the cell with an agent capable of inhibiting the expression or function of Men1 gene or its encoded proteins, thereby reducing p18$^{Ink4c}$ and p27$^{Kip1}$, resulting in induction of CDK2 activity.

In one embodiment, menin regulation of CDK2 and its inhibitors is used for rational drug design of the agents used in the methods and compositions described herein. In another embodiment, the ability of menin to regulate other proteins' expression or function is used for rational drug design (RDD) of agents used in the methods and compositions described herein. In one embodiment, RDD includes not only knowing or predicting the conformation of a desired protein, but also being able to control and predict the conformation of a drug peptide that is to interact with the target protein.

In one embodiment, "primary structure" as used herein refers to one wherein the number and precise sequence of amino acids in the polypeptide is known. The peptide linkage between each of the amino acid residues is implied, but no other forces or bonds are indicated by use of the term "primary structure". In another embodiment, "secondary structure" refers to the extent to which a polypeptide chain possesses any helical, β-sheet or other stable structure. A secondary structure will have a set of angles, $\phi_i$, $\Psi_i$ for each residue i of the chain. "Tertiary structure" refers, in one embodiment, to the tendency for the polypeptide to undergo extensive coiling or folding to produce a complex three-dimensional structure. "Quaternary structure" refers, in another embodiment, to the degree of association between two or more polypeptides, e.g., between two tertiary structures, such as a target protein and a candidate drug or ligand.

In one embodiment, the invention provides a method to identify an antagonist ligand to menin, comprising: contacting menin with a candidate antagonist ligand, under conditions wherein, in the absence of said candidate antagonist ligand, said menin is active; detecting concentration or activity of menin or at least one protein that is regulated by menin when said menin is active, wherein reduction in concentration or activity of said menin or at least one menin-regulated protein in the manner associated with activation of said menin indicates that said candidate antagonist ligand is a menin antagonist.

In one embodiment, the term "antagonist" or "antagonist ligand" refers to a compound that selectively inhibits or decreases function of menin or normal regulatory expression or function of other proteins affected by menin. An antagonist can act in other embodiments by any antagonistic mechanism, such as by binding to menin or to menin-regulated products, thereby inhibiting binding between menin and its regulated products. A menin antagonist can also act indirectly, for example, by modifying or altering the native conformation of menin or menin-regulated products. The methods described herein can advantageously be used to identify a menin antagonist that acts through any antagonistic mechanism.

In one embodiment, the at least one protein that is regulated by menin when said menin is active is histone methyltransferase MLL (mixed lineage leukmeia), MLL-associating proteins, ASHL-2, menin-interacting histone deacetylases, CDK2, p18$^{Ink4c}$, p27$^{Kip1}$ or a combination thereof. In one embodiment, the antagonist identified using the methods described herein, is used in compositions for the treatment of type I or type II diabetes. In another embodiment, the candidate antagonist ligand is a chemical compound from natural products including herbs and fungi, a chemical compound from a synthesized combinatorial library, a chemical compound of existing chemical identities, or a product of rational drug design.

Initially a potential drug, or candidate antagonist ligand could be obtained by screening a random peptide library produced by recombinant bacteriophage in one embodiment, [Scott and Smith, Science, 249:386-390 (1990); Cwirla et al., Proc. Natl. Acad. Sci., 87:6378-6382 (1990); Devlin et al., Science, 249:404-406 (1990)] or a chemical library. An agent thus selected in another embodiment, could then be systematically modified by computer modeling programs until one or more promising potential drugs are identified. Such analysis has been shown to be effective in the development of HIV protease inhibitors [Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1: 109-128 (1993)].

In one embodiment, computer modeling allows the selection of a finite number of rational chemical modifications, as opposed to the countless number of essentially random chemical modifications that could be made, any one of which might lead to a useful drug. Each chemical modification requires additional chemical steps, which while being reasonable for the synthesis of a finite number of compounds, may become overwhelming if all possible modifications are needed to be synthesized. Thus through the use of a three-dimensional structural analysis and computer modeling, a large number of these compounds can be rapidly screened on the computer monitor screen, and a few likely candidates can be determined without the laborious synthesis of numerous compounds.

According to this aspect of the invention and in one embodiment, the invention provides a method of using a three-dimensional structure of menin protein in a drug screening assay comprising the steps of: selecting a potential drug by performing rational drug design based on said three-dimensional structure, wherein said selecting is performed in conjunction with computer modeling; contacting the potential drug with a first polypeptide comprising an amino acid sequence having at least 75% homology to a first predetermined region of the menin; and detecting the binding affinity of the potential drug with said first polypeptide, whereby a potential drug is selected as a drug if the potential drug binds to said first polypeptide. In another embodiment, the method further comprises contacting the bound potential drug with a second polypeptide comprising an amino acid sequence having at least 75% homology to a second predetermined region of the menin; and detecting the binding affinity of the potential drug with said second polypeptide, whereby a potential drug is selected as a drug if the potential drug binds to said first and second polypeptide.

In another embodiment, the first and second polypeptide comprising an amino acid sequence have at least 80% homology to a first predetermined region of the menin, or 85% homology in another embodiment, or 90% homology in another embodiment, or 95% homology in another embodiment, or 100% homology in another embodiment to a first predetermined region of the menin.

Once a potential drug or antagonist is identified, in one embodiment it either can be selected from a library of chemicals that are commercially available from most large chemical companies including Merck, Glaxo Welcome, Bristol Meyers Squib, Monsanto/Searle, Eli Lilly, Novartis and Pharmacia UpJohn, or in another embodiment the potential drug may be synthesized de novo. As mentioned herein, the de novo synthesis of one or even a relatively small group of specific compounds is reasonable experimentation for rational drug design.

The potential drug can be tested in one embodiment by any standard binding assay (including in high throughput binding assays) for its ability to bind to a menin or fragment thereof. In another embodiment the potential drug or antagonist ligand can be tested for its ability to modulate (either inhibit or stimulate) the regulated activity of menin, or the regulated activity of CDK2, p18$^{Ink4c}$, p27Kip1 or a their combination. When a suitable potential drug is identified, a second NMR, or other proper spectroscopic methods of structural analysis can optionally be performed on the binding complex formed between the menin and the potential drug or antagonist ligand. Computer programs that can be used to aid in solving the three-dimensional structure of menins and binding complexes thereof include QUANTA, CHARMM, INSIGHT, SYBYL, MACROMODE, and ICM, MOLMOL, RASMOL, AND GRASP [Kraulis, J. Appl Crystallogr. 24:946-950 (1991)]. Most if not all of these programs and others as well can be also obtained from the WorldWideWeb through the internet.

RDD has been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods may be used in certain embodiments to selectively isolate and subsequently analyze binding components of mixtures of compounds.

In another embodiment, ACE-ESI-MS, uses affinity capillary electrophoresis to accomplish the separation of noncovalent complexes formed upon mixing a biomolecular target such as menin in one embodiment, with a combinatorial library or mixture of compounds. The biomolecular target is typically incorporated into the capillary so that those ligands present in the combinatorial mixture interact with the target and are retained or slowed down within the capillary. Once separated, these noncovalent complexes are analyzed on-line by ESI-MS to ascertain the structures of the complexes and bound components. In another embodiment, size-exclusion chromatography (SEC) followed by LC/MS or CE/MS analysis is used in the determination of affinity or biological function in the methods described herein. Size exclusion is a method to separate a biopolymer target and its complexes with small molecules members of a combinatorial library. Once isolated by SEC, these complexes are dissociated, under denaturing solution conditions, and finally the binding ligands are analyzed by mass spectrometry.

In one embodiment, Bio-affinity characterization mass spectrometry (BACMS) is used for the characterization of noncovalent interactions of mixtures of ligands and biomolecular targets according to the methods described herein. BACMS involves in one embodiment, the electrospray ionization of a solution containing both the affinity target and a mixture of ligands (or a combinatorial library), followed by trapping of all the ionic species in the FTICR ion-trap. The complexes of interest are then identified in the mass spectrum and isolated by selected-ion accumulation. This is followed by low energy dissociation. or 'heating' to separate the higher binding affinity ligands present in the complex. Finally, collisionally activated dissociation (CAD) is used to provide structural information about the high binding affinity ligand. In one embodiment, using BACMS allows for the time-consuming techniques usually needed for the study of libraries, such as affinity chromatography, using solid supports for separation and purification of the complexes, followed by analysis to characterize the selected ligands, are all combined into one FTICR-MS experiment. In one embodiment BACMS is applied as a research tool to the study of menin targets.

In one embodiment, the first and second predetermined regions or the entire protein of the menin used in the screening methods and RDD described herein, are selected based on the three-dimensional structure of menin. In another embodiment, the predetermined regions are catalytic regions, or binding regions, key structural regions or a combination thereof in other embodiments.

The term "about," as used herein, means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects. In one embodiment, when the subject is human, Men1, the mouse gene encoding menin described herein is interchangeable with MEN1, which encodes menin in humans.

The following examples are presented in order to more fully illustrate the preferred embodiments of the invention. They should in no way be construed, however, as limiting the broad scope of the invention.

EXAMPLES

Materials and Methods

Mouse Breeding, Genotyping, and Excision of the Floxed Men1 Locus

All animal studies were approved by University Laboratory Animal Resources, the University of Pennsylvania committee on animal care, and were carried out in accordance with the mandated standards. Men1$^{\Delta N/\Delta N}$ mice (designated Men1$^{1/1}$; mixed FVB; 129Sv background) were kindly provided by Dr. Francis Collins (National Institute for Human Genome, Research;). The pan-active human UBC9 promoter-driven Cre-ERT2 was introduced into murine fertilized eggs to generate Cre-ER transgenic mice1 using the method of lentiviral transgenesis. Breeding was carried out by crossing Men1$^{1/1}$ and Cre-ER mice. Men1$^{1/1}$; Cre-ER mice were genotyped by PCR using the following primers: P1,5'-cccacatccagtccctcttcagct-3' (SEQ ID NO. 1), P2,5'-aaggtacagcagaggtcacagag-3' (SEQ ID NO. 2), and P3,5'-gacaggattgggaattctctttt-3' (SEQ ID NO. 3). The primers for genotyping Cre-ERT2 were 5'-tacaccaaaatttgcctgcattaccgg-3' (SEQ ID NO. 4), and 5'-ttccatgagtgaacgaacctggt-3' (SEQ ID NO. 5). Men1$^{1/1}$;Cre-ER or Men1$^{+/+}$;Cre-ER mice at 12 weeks of age were first fed with tamoxifen (Sigma, St. Louis, Mo.) at a dose of 200 mg/kg body weight/d for 2 consecutive days, followed by a day off and then for a second 2 consecutive days at the same dose. After 7, 14, and 30 days, the mice were sacrificed for analysis. In total, 22 mice (11 male and 11 female) were analyzed, with the male and female mice randomly distributed between the two groups. Immunofluorescent staining of pancreatic sections. Men1$^{l/l}$;Cre-ER and Men1$^{+/+}$;Cre-ER mice (both tamoxifen-fed) were injected i.p. with 50 mg BrdUrd (Sigma)/kg body weight 2 hours before sacrifice and dissection. Pancreata were isolated and processed for H&E staining and three separate sections from each mouse were stained to quantify area of islets using Metamorph software (Molecular Devices Corporation, Sunnyvale, Calif.). For immunofluorescent staining, a rabbit anti-menin antibody (#80;) and a sheep anti-BrdUrd antibody (#2284, Abcam, Inc., Cambridge, United Kingdom) were used in combination with FITC conjugated antirabbit IgG and TRITC-conjugated anti-sheep IgG secondary antibodies, together with 4',6-diamidino-2-phenylindole (DAPI; 10 μg/mL). Images were captured under a Nikon eclipse E800 fluorescent microscope equipped with a CCD digital camera and the BrdUrd-positive cells among the total DAPI-stained cells per islet were quantified. To co-stain BrdUrd with insulin or glucagon in islet cells, the following antibodies were used: monoclonal rat anti-BrdUrd (BU1/75-ICR1, Accurate Chemical & Scientfic Corp., Westbury, N.Y.), Cy2-conjugated antirat IgG, guinea pig anti-insulin, rabbit antiglucagon (Abcam), FITC-conjugated goat anti-rabbit IgGQ5 (Molecular Probes, Inc., Eugene, Oreg.), and FITC-conjugated goat anti-guinea pig IgG (Abcam).

Men1$^{l/l}$; Pdx1Cre-ER mice were generated by crossing floxsd Menl(Menl$^{l/l}$; Sv129, kindly provided by Francis Collins, National Institute for Human Genome Research) to mice expressing Pdx1Cre-ER (Pdx1Cre-ER in mixed background, a kind gift from Dr. Ben Stanger). Exon 3 to 8 of Men 1 in floxed Menl mice were flanked by two loxP sites. Pdx1Cre-ER, expressed in pancreatic beta cells, is driven by the pancreatic and duodenal homeobox 1 promoter. The Men1$^{l/l}$; Pdx1Cre-ER and littermate control Men1 were generated by crossing Men1$^{l/+}$; Pdx1Cre-ER to Men1$^{l/+}$. Genotyping was performed on tail genomic DNA by PCR. The primer sequences are Forward primer 5'-aaggtacagca-gaggtcacagag-3' (SEQ ID NO. 2); Reverse primer 5'-gaca-ggattgggaattctctttt-3' (SEQ ID NO. 3); 5'-cccacatccagtc-cctcttcagct-3' (SEQ ID NO. 1), for deletion band when used with the Forward primer.

RT-PCR and Real-Time TaqMan PCR.

RT-PCR and real-time TaqMan PCR. Total RNA was extracted from cell lines and pancreata using the RNeasy Mini Kit (Qiagen, Valencia, Calif.). OnestepRT-PCR was done with RNA derived from pancreata using the TitanOne Tube RT-PCR System (Roche, Indianapolis, Ind.) following the instructions of the manufacturer. Real-time TaqMan PCR quantification of gene expression was done with RNA derived from cultured cell lines using TaqMan probes for p18Ink4c (Applied Biosystems, Foster City, Calif.; Mm00483243_ml), p27$^{Kip1}$ (Mm00438167_g1), and GAPDH as an internal control (Mm99999915_g1). Analysis was done using the relative quantification method according to instructions from the ABI.

Plasmid Construction and Production of Recombinant Viruses.

Plasmids for generating recombinant retroviruses were constructed by inserting PCR-amplified human menin cDNA into the BamHI/NotI site of the retroviral vector pMX-puro to generate pMX-menin. The production of recombinant adenoviruses and retroviruses was as previously described. For complementation with wild-type menin, Men1$^{\Delta/\Delta 1}$ cells were seeded on day 0, infected with various retroviruses [including green fluorescent protein (GFP)—expressing retroviruses as a control for infection efficiency on day 1, and switched to fresh medium on day 2 before selection with 2 μg/mL puromycin on day 4.

Generation of MEF Cell Lines and Fluorescence-Activated Cell Sorting Analysis.

MEFs from Men1$^{l/l}$ embryos were isolated on embryonic day 14(E14) and were immortalized using the 3T9 protocol. Briefly, 9×10$^5$MEFs were plated on a 60-mm plate and passaged every 3 days. After 30 to 35 passages, immortalized cells emerged. After immortalization, the cells were infected with adenoviruses expressing either GFP (Ad-GFP) or Cre recombinase (Ad-Cre), generating one control cell line (designated Men1l/l) and two menin-null cell lines (designated Men1$^{\Delta/\Delta 1}$ and Men1$^{\Delta/\Delta 2}$). After two to three passages of Men1 excision, the cells were seeded in MEF medium (22) at a density of 1.5×10$^5$ per 100-mm dish on day 0 for cell cycle analysis. On day 1, cells were switched to medium containing only 0.1% FBS. On day 5, normal MEF medium containing nocodazole (Sigma; 200 ng/mL) was added to cells, releasing them from arrest in G0/G1. At various time points after release, cells were pulsed with 10 mmol/L BrdUrd for 2 hours immediately before harvest and fixation. Cell pellets were processed for double staining with an anti-BrdUrd antibody (PharMingen, San Jose, Calif.) and propidium iodide (10 Ag/mL in PBS; Sigma), followed byanalysis on a FACS Calibur (Becton Dickinson, Franklin Lakes, N.J.). Gating was done to focus on the G1, S, and G2-M populations.

Antibodies and Western Blotting

Whole-cell lysates were prepared with ELB lysis buffer [0.1% NP40, 160 mmol/L NaCl, 50 mmol/L HEPES (pH 7.4), 5 mmol/L EDTA (pH 8.0), 1 mmol/L DTT, 0.2 mmol/L phenylmethylsulfonyl fluoride; ref. 24] supplemented with protease inhibitor cocktail set (Calbiochem, San Diego, Calif.) and subjected to Western blotting analysis as previously described (22). The primary antibodies used were rabbit anti-menin (BL-342, Bethyl Lab, Montgomery, Tex.), goat anti-actin (C-11, Santa Cruz Biotechnology, Santa Cruz, Calif.), mouse anti-p27$^{Kip1}$ (BD Transduction, San Jose, Calif.), rabbit anti-p18 (N-20), rabbit anti-p21 (C-19), and rabbit anti-p16 (M-156; Santa Cruz Biotechnology). CDK kinase assays. Cells were lysed in ELB lysis buffer and the lysates (250 μg) were immunoprecipitated by 5 μg of anti-mouse CDK2 antibody (Santa Cruz Biotechnology) or control rabbit IgG. Immunoprecipitates were incubated with 2 μg histone H1 (Upstate Biotech, Norcross, Ga.) and 5 μCi γ-$^{32}$P ATP for 30 minutes before SDS-PAGE separation, as previously described (25), and subjected to phosphoimaging analysis and quantification. Total histone substrate was visualized by Coomassie blue staining. Statistical analysis and quantification. Microsoft Excel and GraphPadPrism software were used to prepare graphs and for statistical analyses. When appropriate, the Student's t test was used to determine significance of results.

High Fat Diet-Induced Obesity and Blood Glucose Intolerance.

C57BL16J mice, Men1$^{l/l}$; Pdx1Cre-ER and control Men1 mice aged at 4 to 6 week were fed either high fat diet (HFD, 60% of calories from fat; D12492; Research Diets, Inc.) or regular chow (Harland) for 13 to 16 weeks. Body weights were followed weekly or biweekly on all mice. Glucose tolerance tests (GTTs) were performed at the beginning and during the last week of feeding.

Excision of the Floxed Men1Locus Using Tamoxifen.

Sixteen weeks after on high fat or normal chow diet Men1$^{l/l}$; Pdx1Cre-ER and their littermate control Men1$^{l/l}$ mice were fed tamoxifen, which was given by gavage at a dose of 200 mg/kg body weight for two consecutive days, followed by one day off and then for another two consecutive days.

Physiological Measurements

Blood glucose values were determined on tail venous blood using an automated glucose monitor (ONETOUCH ULTRA blood Glucometer Elite; Bayer). Serum insulin levels were measured by Ultra Sensitive Mouse Insulin ELISA kit (Crystal Chem. Inc., Downers Grove, Ill., USA). GTTs and acute insulin secretion tests were performed on mice fasted overnight for 16 hours. For GTTs, glucose levels were measured from tail blood collected immediately before (time 0) and 15, 30, 60, 90 and 120 minutes after i.p. injection of glucose (2 g/kg body weight). For acute insulin secretion tests, blood samples were collected before (time 0), 5, 15 minutes after i.p. glucose injection (3 g/kg body weight). Insulin tolerance tests (ITT) was performed on mice fasting for 6 hours and blood glucose levels were determined immediately before (time 0) and 15, 30, and 60 minutes after injection of human regular insulin (0.75 U/kg body weight).

Statistical Analysis

Results FIGS. 13-15 are expressed as mean±SEM. For two-group comparison, the unpaired Student t test was used; for four-group comparison, one-way ANOVA was applied. P values less than 0.05 were considered significant.

Example 1

Ablation of Men1in vitro Increases Cell Proliferation and Transition from G0/G1 to S Phase MEFs from mouse embryos were immortalized with the floxed Men1 using the 3T9 protocol, and then infected the cells with recombinant adenoviruses expressing either GFP (Ad-GFP) or Cre (Ad-Cre) that could excise the floxed Men1 from the genome. The cell lysates from the infected cells were subjected to Western blotting analysis. Ad-Cre (lanes 2 and 3), but not Ad-GFP (lane 1), abrogated expression of menin (FIG. 1A). Men1 excision was also confirmed by genotyping (FIG. 1B) because Men1 excision yielded a PCR fragment of the increased size. The Men1$^{\Delta/\Delta 1}$ cells and the Men1$^{\Delta/\Delta 2}$ cells, two independent pools of the MEFs infected by Ad-Cre, proliferated more quickly than the menin-expressing Men1$^{l/l}$ cells (2.7 and 2.9×10$^6$ versus 1.3×10$^6$ cells; P<0.03, Men1$^{l/l}$ versus Men1$^{\Delta/\Delta}$1; P<0.02, Men1$^{l/l}$ versus Men1$^{\Delta/\Delta}$2; FIG. 1C). To further confirm this difference in cell proliferation in vitro, Men1$^{l/l}$ was excised from one additional independent clone and similar results were obtained.

Figure 2B:
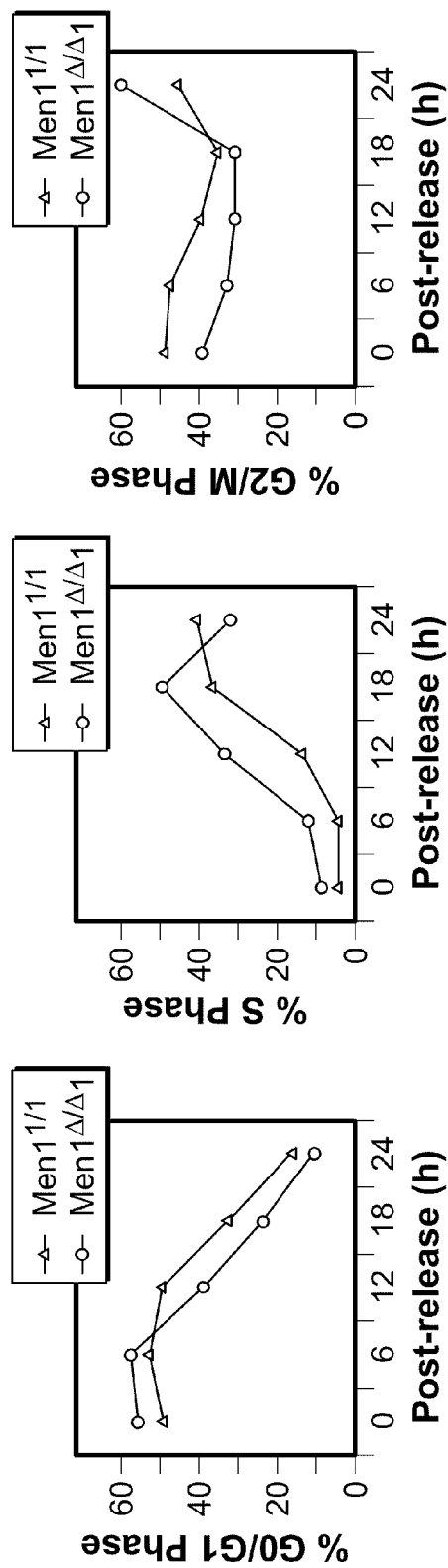

Determination was then made as to whether menin inhibits cell cycle progression and, if it does, at what phase. Serum-starved menin-null or menin-expressing cells were stimulated by addition of serum and allowed to progress for various periods of time up to 24 hours. Cells were harvested at various time points after release and processed for staining with anti-BrdUrd antibody and propidium iodide, followed by flow cytometry analysis. Following serum removal, Men1$^{l/l}$ cells were distributed at G0/G1 (48%) and G2-M (48.1%), with only 3.9% of the cells in S phase (FIG. 2A, top left) as compared with that of asynchronous cells (55%). Similarly, Men1$^{\Delta/\Delta 1}$ cells were primarily distributed in G0/G1 and G2-M phases, with only 7.5% cells in S phase (FIG. 2A, bottom left). Twelve hours after release from serum starvation, only 12.2% of the Men1$^{l/l}$ cells progressed from G0/G1 to S phase (FIG. 2A, top middle). In contrast, 32% of Men1$^{\Delta/\Delta 1}$ cells entered S phase (FIG. 2A, bottom middle). At 24 hours of release, 41.5% of Men1$^{l/l}$ cells reached S phase (top right), whereas only 28% of the Men1$^{\Delta/\Delta}$1 cells were in S phase, as they had already passed their peak at S phase (18 hours) and progressed to G2-M (FIG. 2A, bottom right). The detailed kinetics of cell cycle progression for both Men1$^{l/l}$ cells and Men1$^{\Delta/\Delta}$1 cells are shown in FIG. 2B. These results show that loss of menin expression accelerates progression from G0/G1 to S phase.

Example 2

Ablation of Men1Increases Cdk2 Activity But Decreases p18$^{Ink4c}$ and p27$^{Kip1}$ RNA and Protein Levels The cell cycle is positively regulated by various CDKs and CDK2 plays a crucial role in controlling G0/G1 to S transition. Thus, a determination whether menin inhibits CDK2 activity was made. Lysates from Men1$^{l/l}$ cells and Men1$^{\Delta/\Delta}$1 cells, at various time points of cell cycle progression, were immunoprecipitated with an anti-CDK2 antibody, and the precipitated kinase activity was detected using histone H1 as a substrate. FIG. 3A (top) shows that CDK2 activity, as indicated by the amount of phosphorylation of histone H1, increased after Men1 was excised (lanes 5-7). Quantification of phosphorylation shows that the CDK2 activity was 2-fold higher in Men1$^{\Delta/\Delta}$1 cells than in Men1$^{l/l}$ cells at each corresponding time point (FIG. 3A, bottom). Menin expression did not alter the phosphorylation of the inhibitory Y15 residue nor the activating T160 residue of CD 2 This result suggests that loss of menin expression increases the CDK2 activity and promotes G0/G1 to S transition.

Figure 3D:
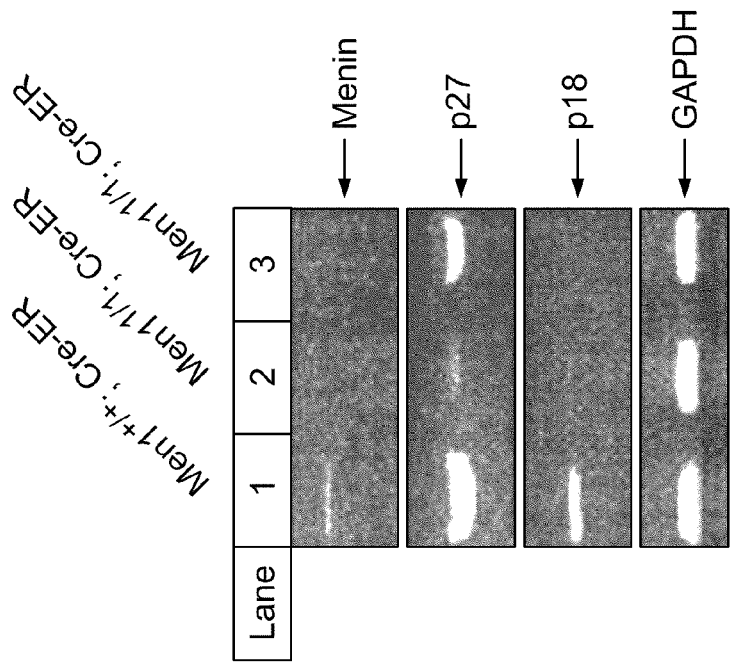
Figure 3C:
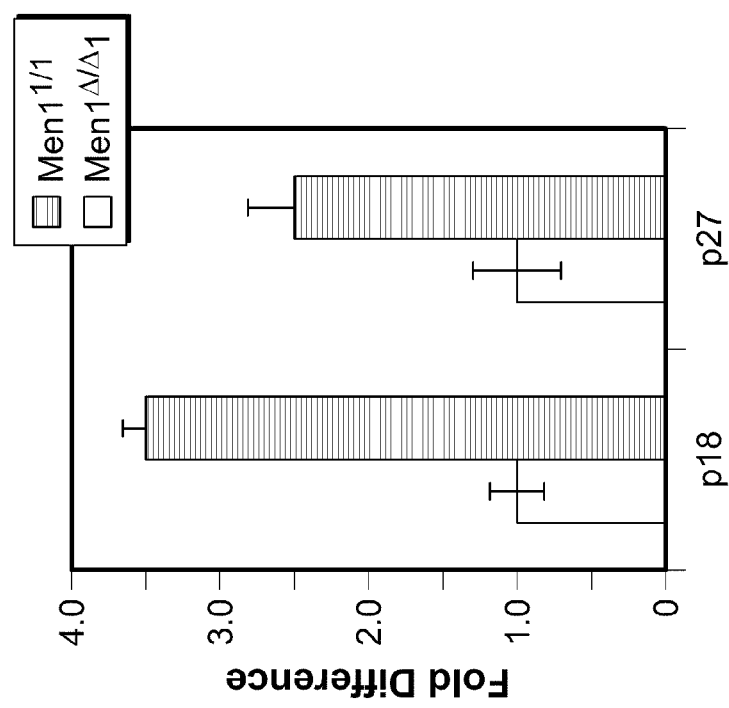

Because the CDK inhibitors p18$^{Ink4c}$ and p27$^{Kip1}$ are implicated in menin-mediated repression of cell proliferation in transformed MEFs and p18$^{Ink4c}$ and p27$^{Kip1}$ proteins inhibit CDK2 activity, it was determined whether menin regulates expression of various CDK inhibitors in the untransformed cells. Men1$^{l/l}$ and Men1$^{\Delta/\Delta}$1 cells were both released from serum starvation and then monitored for 24 hours for expression of various CDK inhibitors using Western blotting analysis. Men1$^{l/l}$ cells expressed menin whereas Men1$^{\Delta/\Delta}$1 cells lost menin expression as expected (FIG. 3B). Expression of both p18$^{Ink4c}$ and p27$^{Kip1}$ was higher in Men1$^{l/l}$ cells than in Men1$^{\Delta/\Delta}$1 cells (FIG. 3B). In contrast, the expression levels of p21$^{Cip1}$ and p16$^{Ink4c}$ were comparable between Men1$^{l/l}$ and Men1$^{\Delta/\Delta}$1 cells (FIG. 3B). In addition, the mRNA levels of p18$^{Ink4c}$ and p27$^{Kip1}$ in Men1$^{l/l}$ cells are 2.5-fold (P<0.02) and 3.5-fold (P<0.001) higher, respectively, than in Men1$^{\Delta/\Delta}$1 cells (FIG. 3C). Although menin-dependent transcription of p18$^{Ink4c}$ and p27$^{Kip1}$ was recently reported, this is the first time that menin was shown to suppress cell cycle progression, repress CDK2 activity, and up-regulate p18$^{Ink4c}$ and p27$^{Kip1}$ in a well-controlled system. These data suggest that menin regulates CDK2, at least in part, by regulating p18$^{Ink4c}$ and p27$^{Kip1}$.

Example 3

Figure 4C:
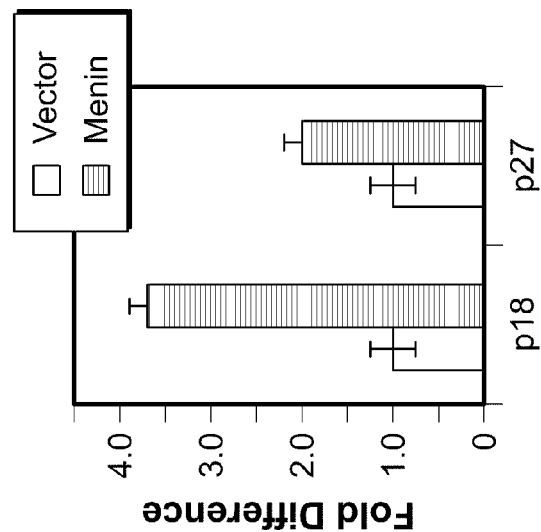
FIG. 4 shows that complementation of Men1$^{\Delta/\Delta1}$ cells with wild-type menin inhibits cell proliferation and restores p18$^{Ink4c}$ and p27$^{Kip1}$ protein and RNA levels. A, Men1$^{\Delta/\Delta1}$ cells were complemented with vector control retroviruses or retroviruses expressing menin. The resulting cell lines were seeded in triplicate on day 0 and counted on day 4 as described in FIG. 1C. This is representative of two independent experiments. B, Western blotting analysis of cell lines indicates that complementation with menin results in increased p27$^{Kip1}$ and p18$^{Ink4c}$ protein levels. C, complementation with menin results in increased p27$^{Kip1}$ and p18$^{Ink4c}$ RNA levels. Real-time TaqMan PCR analysis was carried out using TaqMan probes for p18$^{Ink4c}$, p27$^{Kip1}$, and GAPDH. D, complementation with retroviruses expressing menin represses transition from G0/G1 to S phase. As in FIG. 2A, serum-starved cells were released for various periods of time to monitor cell cycle progression. E, cell cycle profiles were determined at multiple time points as indicated, as described in FIG. 2.
Figure 4B:
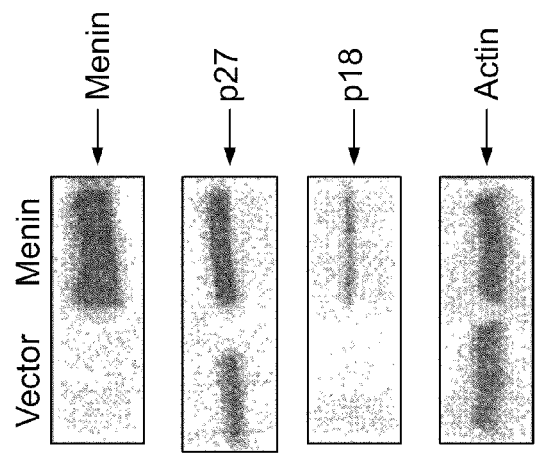
Figure 4A:
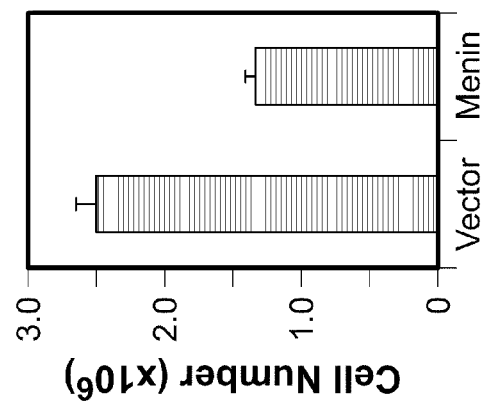

Complementation of Men1$^{\Delta/\Delta}$1 Cells with Wild-Type Menin Inhibits Cell Proliferation and G0/G1 to S Phase Progression and Restores p18$^{Ink4c}$ and p27$^{Kip1}$ Protein and RNA Levels If Men1 excision leads to enhanced cell proliferation and G0/G1 to S phase transition, complementation of menin-null cells with menin should suppress cell proliferation and G0/G1 to S phase progression. Thus, Men1$^{\Delta/\Delta}$1 cells was infected with control vector retroviruses or retroviruses encoding wild-type menin, and the resulting cells were monitored for cell growth, expression of p18$^{Ink4c}$ and p27$^{Kip1}$, and G0/G1 to S progression. By day 4, there were 2.5×10$^6$ vector-complemented cells versus 1.3×10$^6$ menin-complemented cells (FIG. 4A); these differences were significant (P<0.0006). In addition, expression of p18$^{Ink4c}$ and p27$^{Kip1}$ was higher in menin-complemented cells than in vector complemented cells at both the protein and mRNA (FIGS. 4B and C) levels, consistent with a previous report that menin is crucial for optimal expression of p27$^{Kip1}$ (P<0.003) and p18$^{Ink4c}$ (P<0.0002).

Figure 4D:
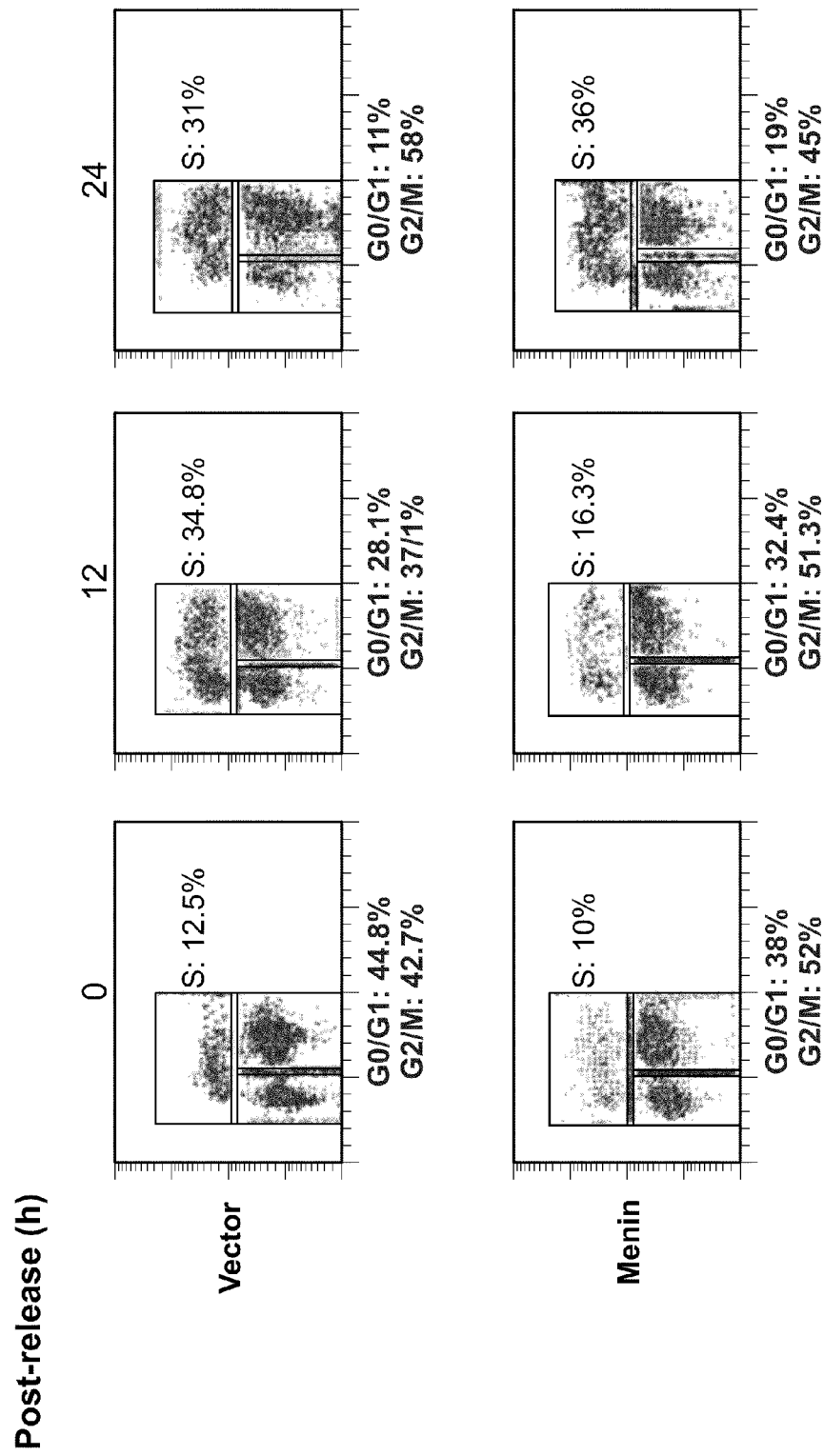
Figure 4E:
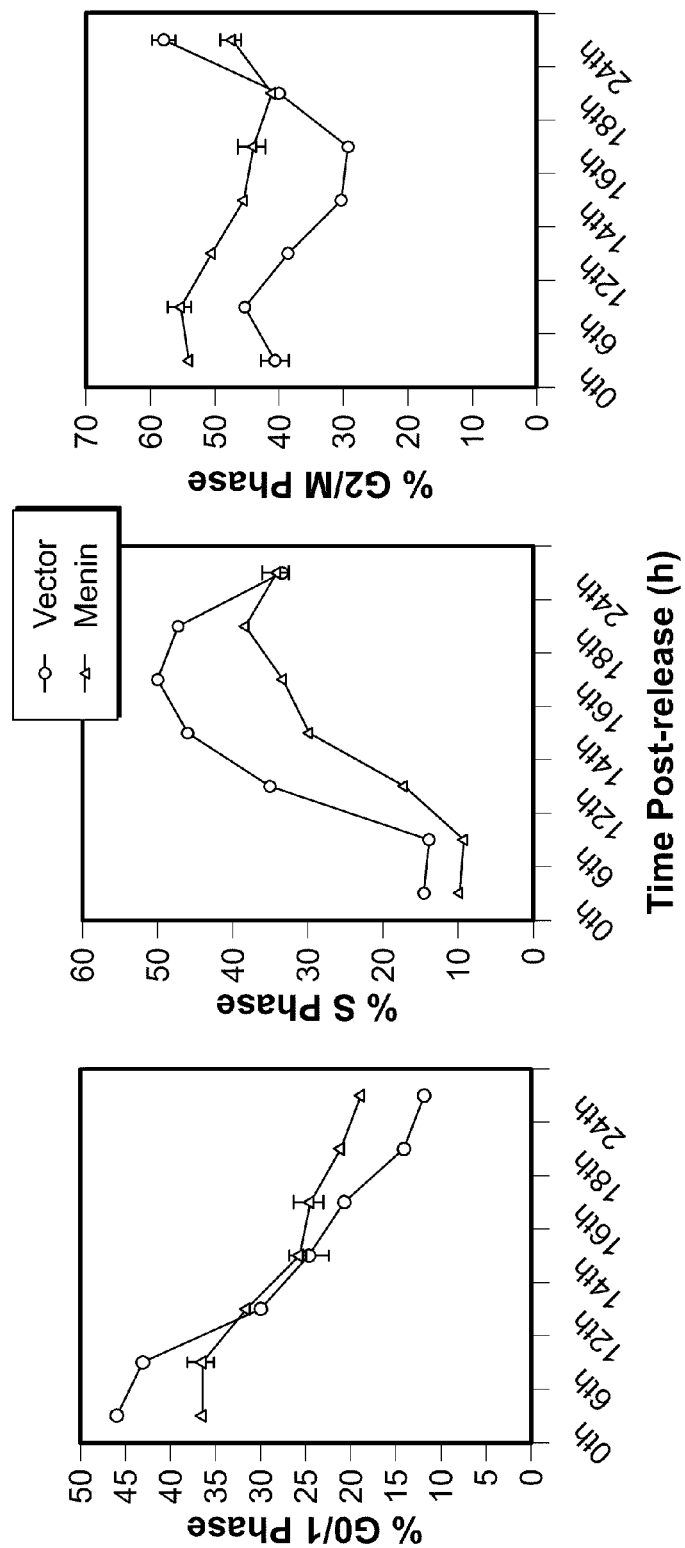

To further confirm the crucial role of menin in regulating cell cycle progression, the issue of whether complementing cells with menin can rescue the role of menin in suppressing transition from G0/G1 to S phase was tested. Following serum starvation, 12.5% of vector-complemented cells and 10% of menin-complemented cells were in S phase (FIG. 4D). Notably, 12 hours after release, 33% of vector-complemented cells were in S phase, as compared with 16% in menin-complemented cells (FIG. 4D). Twenty-four hours after release, vector-complemented cells progressed out of the peak of S phase (31%) whereas a greater percentage of menin-complemented cells remained in S phase (36%; FIG. 4D). A more detailed cell cycle profile at multiple time points after release further supports the role of menin in slowing down G0 to S phase transition (FIG. 4E).

Example 4

Men1 Excision in Pancreatic Islets Acutely Results in Increased Islet Cell Proliferation and Size The above examples in cultured cells show a crucial role for menin in controlling S-phase entry. However, it is still unclear whether this role of menin also applies to in vivo endocrine cells such as pancreatic islet cells, in which a germ-line mutation in only one Men1 allele predisposes the patient to the development of islet cell hyperplasia. In addition, because it takes 6 months for mice carrying a Men1 mutation to develop insulinomas, which have a high proliferation index, an important unresolved question is whether time-controlled Men1 excision can quickly lead to enhanced proliferation of pancreatic islet cells. To address these questions, mice were bred with the Men1 locus flanked by lox P sites (Men1$^{l/1}$, previously Men1$^{\Delta N/\Delta N}$) with mice (Men1$^{+/+}$) expressing Cre-ER (estrogen receptor) driven by a pan-active UBC9 promoter, to generate mice with the Men1$^{l/l}$; Cre-ER genotype. Cre-ER expressed from a transgene can be activated by tamoxifen, resulting in excision of genes flanked by lox P sites. Both control mice (Men1$^{+/+}$) expressing Cre-ER and the Men1$^{l/l}$;Cre-ER mice were fed with tamoxifen, and then pancreata were harvested to determine excision of the conditional Men1 locus. Tamoxifen effectively induced Men1 excision in the pancreata of the Men1$^{l/l}$;Cre-ER mice (FIGS. 5A and B, lane 2), but not in Men1$^{+/+}$;Cre-ER mice (FIG. 5B, lane 1). Conversely, in the absence of tamoxifen, the floxed Men1 remained intact in the pancreata of Men1$^{l/l}$;Cre-ER mice, indicating no leakiness in excision of the Men1 locus in the absence of tamoxifen (FIG. 5B, lane 3). Given the effective control of Men1 excision, further experiments were done using Men1$^{+/+}$;Cre-ER and Men1l/l;Cre-ER mice to control for any nonspecific effects of tamoxifen treatment.

Figure 5N:
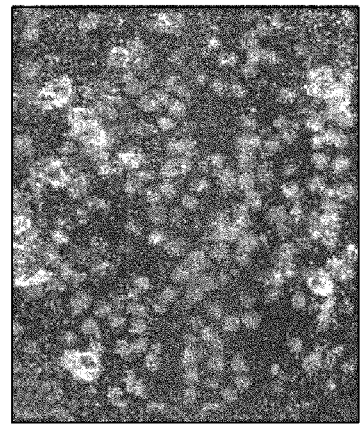
Figure 5O:
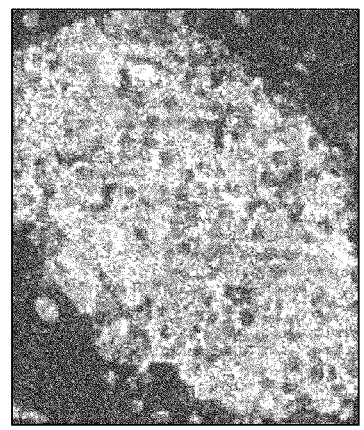
Figure 5K:
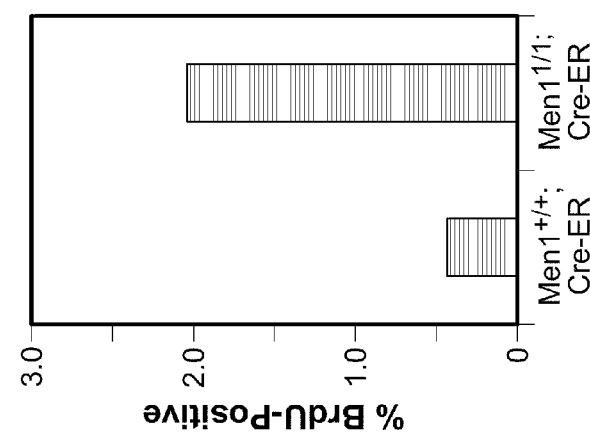

To detect islet cell proliferation after Men1 excision, BrdUrd was injected into Men1$^{+/+}$;Cre-ER and Men1l/l;Cre-ER 1 month after the tamoxifen treatment. Pancreata from the mice were processed for staining with anti-menin and anti-BrdUrd antibodies to determine the relationship between Men1 excision and BrdUrd uptake by pancreatic islet cells. Islet cells from the Men1$^{+/+}$;Cre-ER mice expressed menin (FIG. 5C) but contained only one BrdUrd positive cell (FIGS. 5D and F). In addition, menin seemed to be expressed preferentially in islet cells as compared with the adjacent exocrine cells (FIG. 5C). In contrast, islet cells from Men1l/l;Cre-ER mice largely lost menin expression but contained multiple BrdUrd positive cells (FIGS. 5G, H, and J). Quantification of the BrdUrd positive cells from islets of multiple mice indicates that 0.4% of islet cells were BrdUrd positive in Men1$^{+/+}$;Cre-ER mice, but notably 2.0% of cells were BrdUrd positive in Men1l/l;Cre-ER mice (FIGS. 5H and K; P<0.008). To determine whether the BrdUrd-positive cells are either insulin-secreting β-cells or glucagon-secreting α-cells, pancreatic sections were co-stained with the anti-insulin antibody or the anti-glucagon antibody. In the islet from tamoxifen-fed Men1l/l;Cre-ER mice, there were two BrdUrd-positive cells, both co-stained with the anti-insulin antibody (red in the nucleus, FIG. 5N). Conversely, BrdUrd-positive cells were not co-stained with the anti-glucagon antibody (FIG. 5O). Together, these results indicate that Men1 excision leads to increased proliferation of islet cells including β cells well before the development of insulinomas. These results further support the in vitro results that menin represses G0/G1 progression or S-phase entry of cultured cells (FIG. 2).

To extend the in vitro findings about the role of menin in upregulating p27$^{Kip1}$ and p18$^{Ink4c}$ to in vivo organs such as pancreatic islets, the effect of loss of Men1 on p27$^{Kip1}$ and p18$^{Ink4c}$ expression was also determined in the murine pancreata. Pancreata were harvested from Men1$^{+/30}$;Cre-ER and Men1l/l;Cre-ER mice that were fed with tamoxifen. Quantification of various mRNAs from the pancreata by RT-PCR shows that Men1 expression was detectable in Men1$^{+/+}$;Cre-ER mice (FIG. 3D, top, lane 1) but greatly reduced in Men1l/l;Cre-ER mice (lanes 2 and 3). Similarly, expression of p27$^{Kip1}$ and p18$^{Ink4c}$ was also markedly decreased in Men1l/l;Cre-ER mice, as compared with the control mice, whereas expression of control GAPDH was comparable between Men1$^{+/+}$;Cre-ER and Men1l/l;Cre-ER mice (FIG. 3D). These data support the notion that menin regulates p27$^{Kip1}$ and p18$^{Ink4c}$ levels in vivo.

Figure 6A:
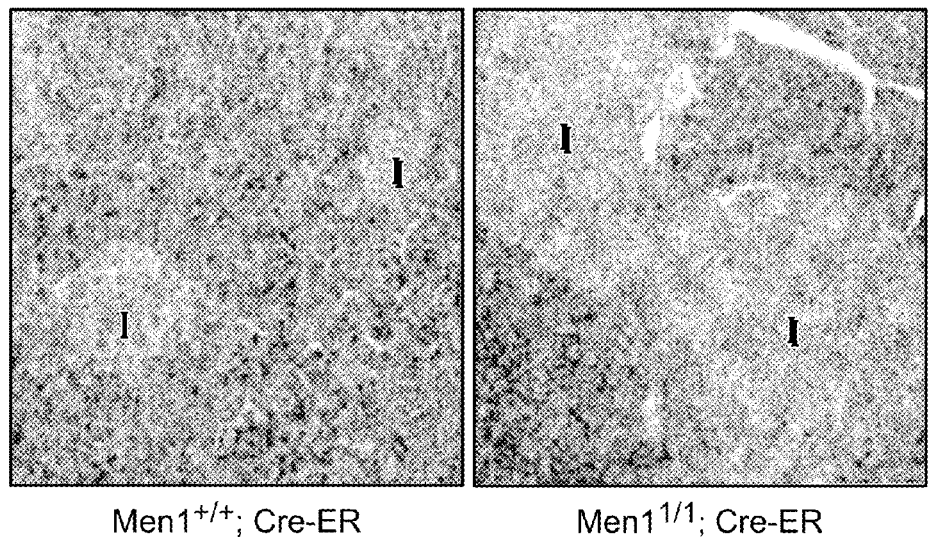
FIG. 6 shows that excision of the floxed Men1 results in enlargement of pancreatic islets. A) enlargement of pancreatic islets after excision of Men1. H&E staining of pancreatic sections prepared from tamoxifen-fed Men1$^{+/+}$;Cre-ER and Men1$^{1/1}$;Cre-ER mice 1 month after tamoxifen treatment. Images were acquired using 20" objective lens. I) islets. B, quantification of the size of islets derived from three Men1$^{+/+}$;Cre-ER and four Men1$^{1/1}$;Cre-ER mice as described in Materials and Methods. Circles, value of the area for a single islet in arbitrary units. Line, mean of areas of all the measured islets.
Figure 6B:
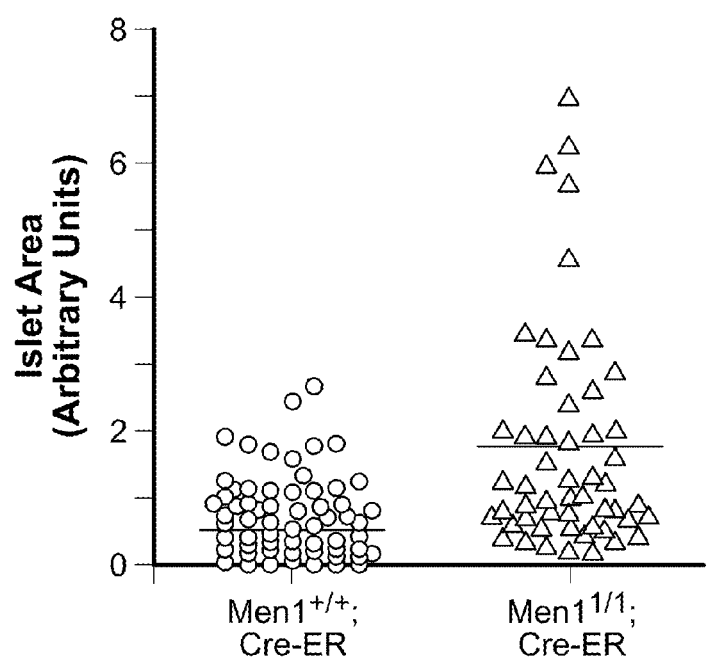

Enhanced islet cell proliferation after Men1 excision may affect the size of the islets after certain period of enhanced proliferation. Notably, the size of islets from Men1l/l;Cre-ER mice was, on average, larger than that of the control mice 1 month after tamoxifen treatment (FIG. 6A). The mean of the area of the islets from the Men1l/l;Cre-ER mice was ~3.5-fold larger than that from the control mice (FIG. 6B, 0.50 versus 1.73, P<0.0001). Collectively, these results indicate that deletion of Men1, within a month, leads to enhanced cell proliferation and enlargement of pancreatic islets, a tissue affected in MEN1 syndrome.

To further determine how soon after Men1 deletion BrdUrd uptake increases in islet cells, pancreata were further examined at 7 and 14 days following tamoxifen treatment. At 7 days, ~0.2% of islet cells in Men1$^{+/+}$;Cre-ER mice were BrdUrd positive in comparison with 0.6% of islet cells in Men1l/l;Cre-ER mice (FIG. 7A, P<0.005), indicating a significant increase in islet cell proliferation 7 days after Men1 excision. At 14 days, 0.2% of islet cells from control mice were BrdUrd positive as compared with 1.4% of islet cells in Men1 l/l;Cre-ER mice (FIG. 7A, P<0.4×10$^5$). The mean islet area was not significantly different between Men1$^{+/+}$; Cre-ER and Men1l/l;Cre-ER mice on day 7. However, on day 14, the mean of the area of the islets from the Men1l/l;Cre-ER mice was ~1.5-fold larger than that from the control mice (FIG. 7B, 0.84 versus 1.22, P<0.005). These results strongly suggest that deletion of Men1 acutely results in increased cell proliferation, which may accelerate the accumulation of islet cells, resulting in islet enlargement and hyperplasia 14 days after Men1 excision.

Figure 9:
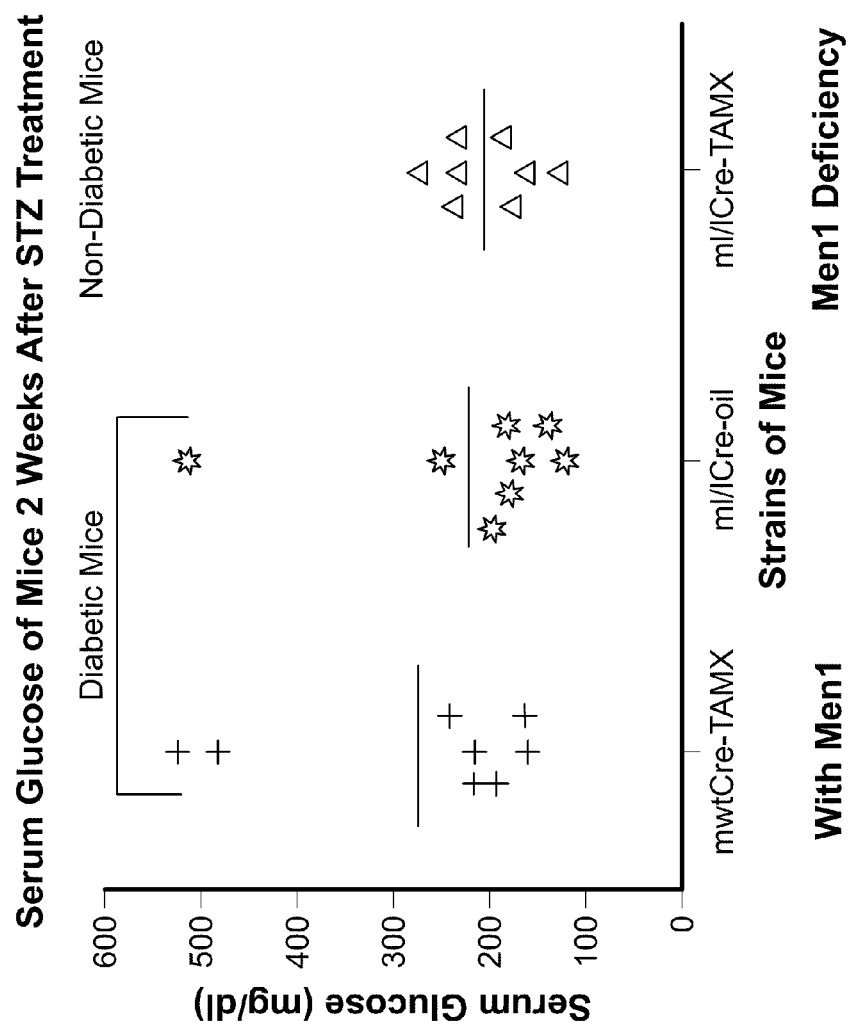
FIG. 9 shows the results for STZ induction of diabetes as in FIG. 8, taken once a week for 2 weeks, starting a week after the last STZ injection. Serum glucose was tested for each sample.
Figure 10B:
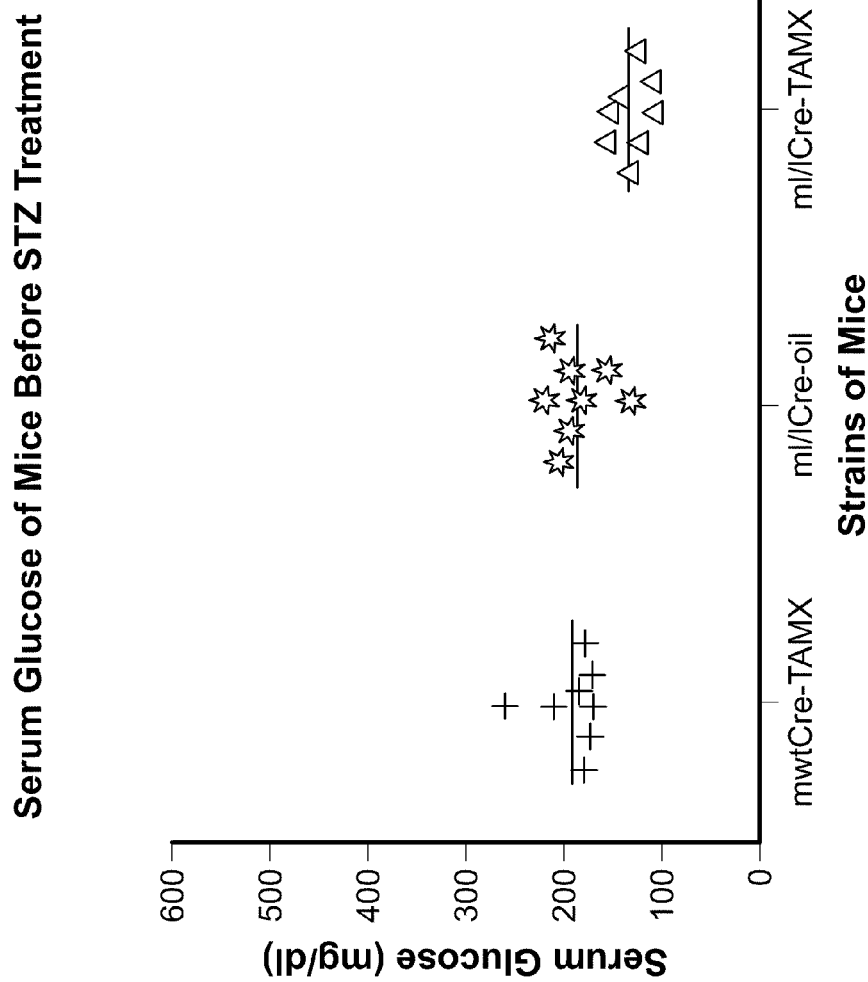
FIG. 10 shows non-fasting blood collected before STZ injection (A) and serum glucose levels in all mice of the three groups shown below 300 mg/dl (B).

Results for half year old mice, which were divided into three groups: Men1$^{1/1}$, Men1$^{+/+}$;Cre-ER, and Men1$^{1/1}$;Cre-ER are shown in FIGS. 8 and 9. The mice in the last two groups were fed with tamoxifen at 200 μg/gbw/day for 4 days. Men1$^{1/1}$ mice were fed with corn oil as the control. One month after the last dose of tamoxifen or corn oil, multiple low-dose of streptozotocin (STZ, 40 mg/kg body weight in citrate buffer, pH 4.0) was injected intraperitoneally once a day for 5 consecutive days. Non-fasting blood was collected before STZ injection, and serum gluclose levels in all mice of the three groups were below 300 mg/dl (FIG. 10). However, 2 weeks after the last STZ injection serum glucose levels in 3 mice of the two control groups reached a level close to 500 mg/dl, yet none of mice with excised Men1 showed abnormally high glucose level (FIG. 11). Thus, the results show that reduced expression or function of the Men1 gene, can cause reduction in the levels of serum glucose following the inducement of diabetes due to STZ injection or reduce the incidence or onset of diabetes induced by STZ.

Figure 11A:
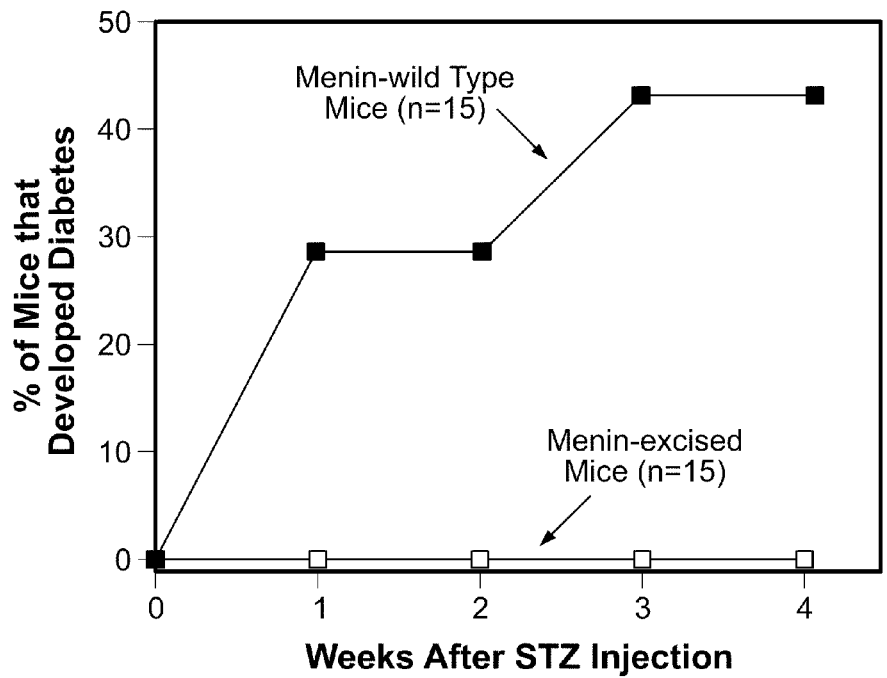
FIG. 11a shows Men1 excision causes resistance to streptozotocin (STZ)-induced Type 1 diabetes. Men1$^{1/1}$ (menin-wild type, n=15) and Men1$^{1/1}$;Cre-ER (menin-excised, n=15) male mice (6 months old) were fed with tamoxifen at 200 μg/g body weight per day for 4 days. One month after the last dose of tamoxifen, multiple low doses of STZ, 40 mg/kg body weight in citrate buffer (pH 4.0), were injected intraperitoneally once a day for 5 consecutive days. Nonfasting blood was collected before STZ injections, and serum glucose levels in all mice were below 250 mg/dl. However, 2 weeks after the last STZ injection, serum glucose levels of multiple menin-wild type mice reached >400 mg/dl, yet none of mice with excised Men1 (menin-excised) showed abnormally high glucose levels.

As shown in FIG. 11a, approximately 50% of menin-expressing mice developed diabetes induced by streptozotocin (STZ), a drug that specifically damages pancreatic insulin-secreting β-cells (FIG. 11a). In contrast, none of mice in which the Men1 gene was excised developed diabetes (FIG. 11a). These studies indicate that the increased mass of insulin-secreting β cells in the Men1-excised mice leads to resistance to STZ-induced diabetes.

Example 5

Men1 Excision Reduces High Blood Glucose Levels

Figure 11B:
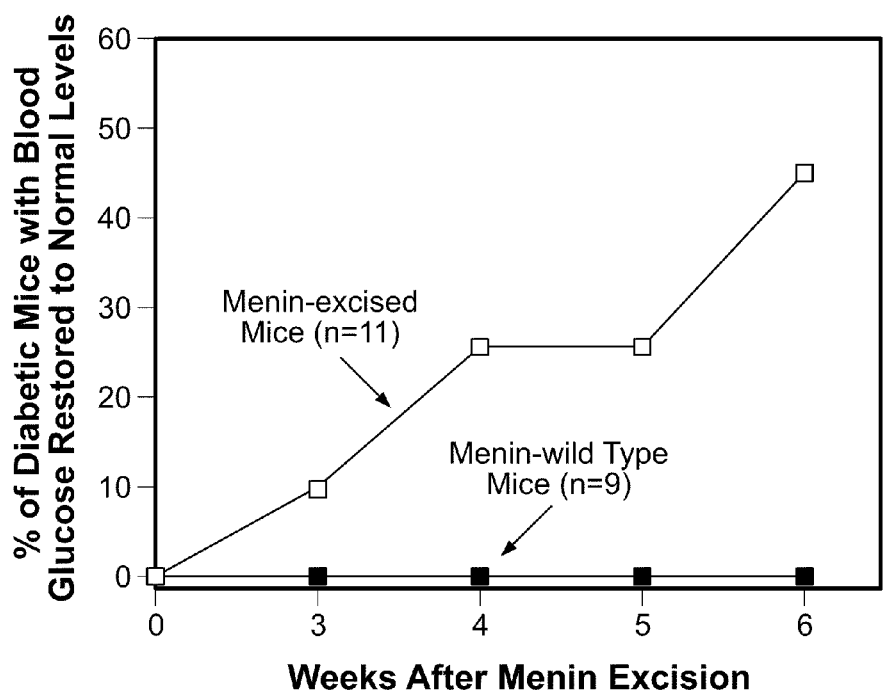
FIG. 11b shows Men1 excision restores the blood glucose levels of diabetic mice to normal range. Men1$^{1/1}$ and Men1$^{1/1}$;CreER male mice were injected intraperitoneally with multiple low doses of STZ at 40 mg/kg in sodium citrate buffer (pH 4.0) for 5 consecutive days to induce diabetes. Blood glucose was monitored once a week for 3 weeks. Mice with blood sugar levels of >400 mg/dl for 2 consecutive weeks were considered diabetic. Three weeks after STZ injections, the diabetic mice from the two groups were fed with tamoxifen at 200 μg/g body weight per day for 4 days. Blood glucose was monitored weekly from the third week after tamoxifen feeding. Nine Men1$^{1/1}$ diabetic mice (menin-wild type) and 11 Men1$^{1/1}$;CreER (menin-excised) diabetic mice were treated with tamoxifen. The unfasting blood sugar level of <250 mg/dl in mice was considered normal, while all the diabetic mice had blood sugar levels of >400 mg/dl. Blood glucose in 50% of menin-excised mice, but none of menin-wild type mice, was restored to the normal range 6 weeks after menin excision.

After diabetes was firmly established in mice using the methods described in the previous examples, Men1 was excised. Six weeks later, blood glucose levels in ~50% of the mice were restored to normal (FIG. 11b). In contrast, none of mice still expressing menin showed any substantial reduction of blood glucose levels (FIG. 11b). These results demonstrate that inhibition of a single protein, menin, can correct the high blood glucose levels in diabetic mice.

Example 6

Figure 12:
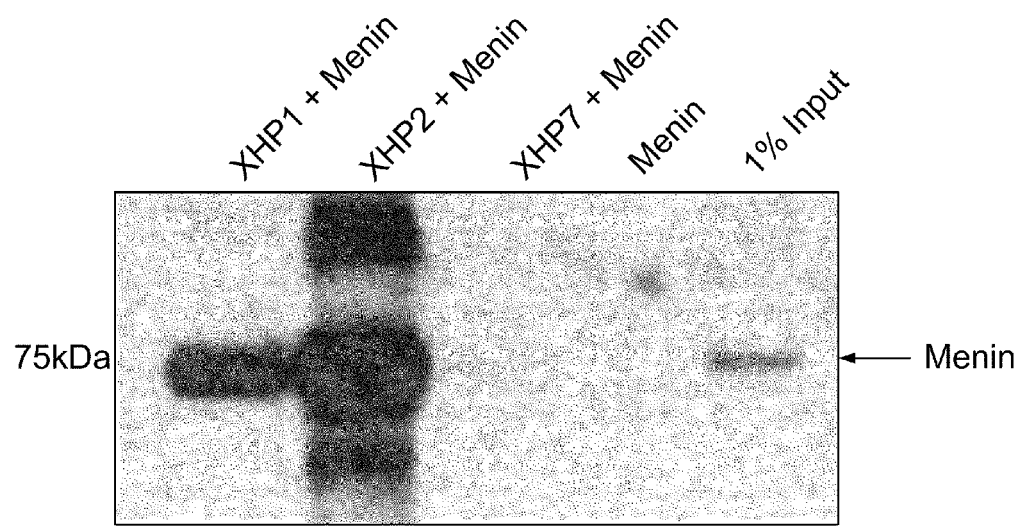
FIG. 12 shows that Menin specifically binds to a short synthetic peptide from the N-terminus of MLL in vitro. Biotinylated peptides were synthesized at the Peptide synthesis facility at Yale University, and loaded to streptavidin-agraose beads (Invitrogen, Inc), and incubated with menin expressed in and purified from E. coli. After multiple washings, the beads were analyzed via Western blot analysis using an anti-menin antibody.

Menin Specifically Binds to a Short Synthetic Peptide from the N-Terminus of MLL in vitro As shown in FIG. 12, Menin specifically binds to a short synthetic peptide from the N-terminus of MLL in vitro.

Biotinylated peptides were synthesized, loaded to streptavidin-agraose beads (Invitrogen Inc), and incubated with menin expressed in and purified from *E. coli*. After multiple washings, the beads were analyzed via Western blot analysis using an anti-menin antibody. As shown in FIG. 12, the peptides comprising MAHSCRWRFP (SEQ ID No.6) were able to react with Men1. Especially, the peptide designated the sequence MAHSCRWRFPGSGSCRWRFP (SEQ ID No. 7).

Example 7

Inhibition of Menin Ameliorates High Fat Diet Associated Diabetes

The inventors of the instant application first examined if menin expression is altered in pancreatic islets in high fat diet induced Type 2 diabetes in C57BL/6J mice, a strain of mice in which obesity, and Type 2 diabetes can be induced. The mice were fed with normal chow diet or high fat diet for over three months, and the high fat diet (HFD)-fed mice gained significant amount of body weight (FIG. 13A) and developed hyperglycemia in glucose tolerance test (GTT) (FIG. 13B). Nevertheless, the levels of menin expression in islets of the chow diet and HFD-fed mice were similar (FIGS. 13C and 13D).

Figures 14A, 14B:
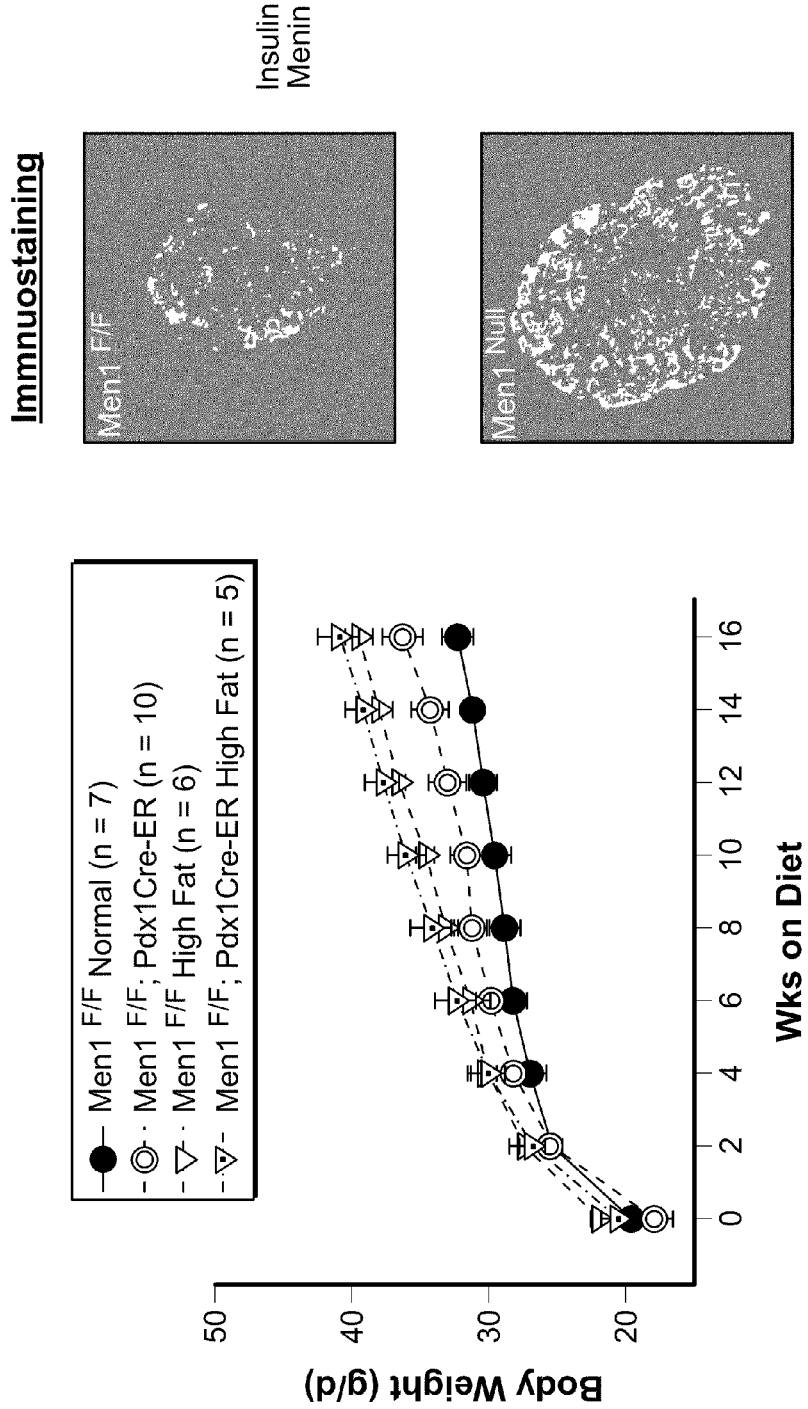
FIG. 14 shows that high fat diet increased body weight in Men1$^{1/1}$;PdxlCre-ER and control mice. A, Men1$^{l/l}$;PdxlCre-ER and control Men1$^{l/l}$ mice (4-week of age, n=7 to 10 mice per group) were fed high fat diet or normal chow diet for 16 weeks age. A, biweekly body weight. B, Men1$^{l/l}$;PdxlCre-ER and control Men1$^{l/l}$ mice (8-week of age, n=5 mice per group) were fed TAM to excise Men1$^{l/l}$ as described in material and methods section. B, immunohistologic detection of menin protein level in pancreatic sections.

To determine if Men1 excision can ameliorate glucose intolerance associated with type 2 diabetes, the Men1 F/F control mice and Men1 F/F; Pdx1-Cre-ER mice were fed with either normal chow diet or HFD. These mice had a mixed genetic background from breeding involving SV129 strain. These mice were monitored biweekly for body weight change and both Men1 F/F and Men1 F/F;pdx-Cre-ER mice gained significant amount of body weight after HFD feeding (FIG. 14A). It was confirmed that the floxed Men1 in Men1 F/F;pdx-Cre-ER mice, but not in control Men1 F/F mice, was excised from the pancreatic islets upon feeding with Tamoxifen, based on immunohistochemistry staining (FIG. 14B).

Glucose tolerance test was performed on the control Men1 F/F mice and Men1 F/F;pdx-Cre-ER mice that were fed with either normal chow diet or HFD for over three months (FIG. 15, left panel). The control Men1 F/F mice and Men1 F/F;pdx-Cre-ER mice on HFD developed severe glucose intolerance, as compared with their counterparts in chow diet (FIG. 15, left panel). Then these mice were fed with tamoxifen. One month after feeding with tamoxifen, and the floxed Men1 was supposed to be excised only from Men1 F/F;pdx-Cre-ER mice, but not from the control Men1 F/F mice. Consistent with the enhanced beta cell and islet function in the Men1 excised mice, the glucose intolerance in tamoxifen-fed diabetic mice was abolished, indicating that Men1 excision-induced beta cell proliferation restore the glucose intolerance in mice (FIG. 15, right panel). Notably, the Men1 F/F; pdx-Cre-ER mice on HFD showed normal glucose levels in glucose tolerance test (FIG. 15, right panel All publications, patents, and patent applications cited herein are hereby incorporated by reference in their entirety for all purposes.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for inducing proliferation of non-cancerous, insulin-secreting pancreatic beta cells, the method comprising the step of transiently contacting non-cancerous, diabetic pancreatic islets or beta cells with an inhibitor of Men1 expression or menin function in an amount and for a time to induce proliferation of non-cancerous, insulin-secreting pancreatic beta cells.

2. The method of claim 1, wherein the contacting step is performed in vitro.

3. The method of claim 2, wherein the inhibitor is siRNA.

4. The method of claim 1, wherein the inhibitor of Men1 expression is a peptide comprising the amino acid sequence represented by SEQ ID NO.'s 6-7.

5. A method for inducing proliferation of non-cancerous, insulin-secreting pancreatic beta cells without inducing tumorigenesis, the method comprising the step of transiently contacting non-cancerous pancreatic islets or beta cells with an inhibitor of Men1 expression or menin function in an amount and for a time to induce proliferation but not tumorigenesis of non-cancerous, insulin-secreting pancreatic beta cells.

* * * * *

UNITED STATES PATENT AND TRADEMARK OFFICE
CERTIFICATE OF CORRECTION

PATENT NO. : 9,550,817 B2
APPLICATION NO. : 12/324473
DATED : January 24, 2017
INVENTOR(S) : Xianxin Hua et al.

It is certified that error appears in the above-identified patent and that said Letters Patent is hereby corrected as shown below:

In the Specification

In Column 1, Line 13, insert the following:
--GOVERNMENT INTEREST STATEMENT
This invention was made with government support under grant number CA113962 and CA100912 awarded by the National Institutes of Health. The government has certain rights in the invention.--

Signed and Sealed this
Nineteenth Day of February, 2019

Andrei Iancu
*Director of the United States Patent and Trademark Office*

SEQUENCE LISTING

<160> NUMBER OF SEQ ID NOS: 8

<210> SEQ ID NO 1
<211> LENGTH: 24
<212> TYPE: DNA
<213> ORGANISM: mouse

<400> SEQUENCE: 1
cccacatcca gtccctcttc agct                                              24

<210> SEQ ID NO 2
<211> LENGTH: 23
<212> TYPE: DNA
<213> ORGANISM: mouse

<400> SEQUENCE: 2
aaggtacagc agaggtcaca gag                                               23

<210> SEQ ID NO 3
<211> LENGTH: 23
<212> TYPE: DNA
<213> ORGANISM: Mouse

<400> SEQUENCE: 3
gacaggattg ggaattctct ttt                                               23

<210> SEQ ID NO 4
<211> LENGTH: 27
<212> TYPE: DNA
<213> ORGANISM: Mouse

<400> SEQUENCE: 4
tacaccaaaa tttgcctgca ttaccgg                                           27

<210> SEQ ID NO 5
<211> LENGTH: 24
<212> TYPE: DNA
<213> ORGANISM: Mouse

<400> SEQUENCE: 5
tttccatgag tgaacgaacc tggt                                              24

<210> SEQ ID NO 6
<211> LENGTH: 10
<212> TYPE: PRT
<213> ORGANISM: Human

<400> SEQUENCE: 6

Met Ala His Ser Cys Arg Trp Arg Phe Pro
1               5                   10

<210> SEQ ID NO 7
<211> LENGTH: 20
<212> TYPE: PRT
<213> ORGANISM: Human

<400> SEQUENCE: 7

Met Ala His Ser Cys Arg Trp Arg Phe Pro Gly Ser Gly Ser Cys Arg
1               5                   10                  15

Trp Arg Phe Pro
            20

<210> SEQ ID NO 8

<211> LENGTH: 615
<212> TYPE: PRT
<213> ORGANISM: Human

<400> SEQUENCE: 8

```
Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Trp Ser Pro Val Gly Thr Lys Leu Asp Ser Ser
145                 150                 155                 160

Gly Val Ala Phe Ala Val Val Gly Ala Cys Gln Ala Leu Gly Leu Arg
                165                 170                 175

Asp Val His Leu Ala Leu Ser Glu Asp His Ala Trp Val Val Phe Gly
            180                 185                 190

Pro Asn Gly Glu Gln Thr Ala Glu Val Thr Trp His Gly Lys Gly Asn
        195                 200                 205

Glu Asp Arg Arg Gly Gln Thr Val Asn Ala Gly Val Ala Glu Arg Ser
    210                 215                 220

Trp Leu Tyr Leu Lys Gly Ser Tyr Met Arg Cys Asp Arg Lys Met Glu
225                 230                 235                 240

Val Ala Phe Met Val Cys Ala Ile Asn Pro Ser Ile Asp Leu His Thr
                245                 250                 255

Asp Ser Leu Glu Leu Leu Gln Leu Gln Gln Lys Leu Leu Trp Leu Leu
            260                 265                 270

Tyr Asp Leu Gly His Leu Glu Arg Tyr Pro Met Ala Leu Gly Asn Leu
        275                 280                 285

Ala Asp Leu Glu Glu Leu Glu Pro Thr Pro Gly Arg Pro Asp Pro Leu
    290                 295                 300

Thr Leu Tyr His Lys Gly Ile Ala Ser Ala Lys Thr Tyr Tyr Arg Asp
305                 310                 315                 320

Glu His Ile Tyr Pro Tyr Met Tyr Leu Ala Gly Tyr His Cys Arg Asn
                325                 330                 335

Arg Asn Val Arg Glu Ala Leu Gln Ala Trp Ala Asp Thr Ala Thr Val
            340                 345                 350

Ile Gln Asp Tyr Asn Tyr Cys Arg Glu Asp Glu Ile Tyr Lys Glu
        355                 360                 365

Phe Phe Glu Val Ala Asn Asp Val Ile Pro Asn Leu Leu Lys Glu Ala
    370                 375                 380

Ala Ser Leu Leu Glu Ala Gly Glu Glu Arg Pro Gly Glu Gln Ser Gln
```

-continued

```
            385                 390                 395                 400
Gly Thr Gln Ser Gln Gly Ser Ala Leu Gln Asp Pro Glu Cys Phe Ala
                405                 410                 415

His Leu Leu Arg Phe Tyr Asp Gly Ile Cys Lys Trp Glu Glu Gly Ser
                420                 425                 430

Pro Thr Pro Val Leu His Val Gly Trp Ala Thr Phe Leu Val Gln Ser
            435                 440                 445

Leu Gly Arg Phe Glu Gly Gln Val Arg Gln Lys Val Arg Ile Val Ser
            450                 455                 460

Arg Glu Ala Glu Ala Ala Glu Ala Glu Glu Pro Trp Gly Glu Glu Ala
465                 470                 475                 480

Arg Glu Gly Arg Arg Arg Gly Pro Arg Arg Glu Ser Lys Pro Glu Glu
                485                 490                 495

Pro Pro Pro Pro Lys Lys Pro Ala Leu Asp Lys Gly Leu Gly Thr Gly
                500                 505                 510

Gln Gly Ala Val Ser Gly Pro Pro Arg Lys Pro Pro Gly Thr Val Ala
            515                 520                 525

Gly Thr Ala Arg Gly Pro Glu Gly Gly Ser Thr Ala Gln Val Pro Ala
            530                 535                 540

Pro Ala Ala Ser Pro Pro Pro Glu Gly Pro Val Leu Thr Phe Gln Ser
545                 550                 555                 560

Glu Lys Met Lys Gly Met Lys Glu Leu Leu Val Ala Thr Lys Ile Asn
                565                 570                 575

Ser Ser Ala Ile Lys Leu Gln Leu Thr Ala Gln Ser Gln Val Gln Met
                580                 585                 590

Lys Lys Gln Lys Val Ser Thr Pro Ser Asp Tyr Thr Leu Ser Phe Leu
                595                 600                 605

Lys Arg Gln Arg Lys Gly Leu
610                 615
```